(12) United States Patent
Cunningham et al.

(10) Patent No.: US 6,206,841 B1
(45) Date of Patent: Mar. 27, 2001

(54) METHOD AND APPARATUS FOR OBTAINING BLOOD FOR DIAGNOSTIC TESTS

(75) Inventors: David D. Cunningham, Lake Villa; Timothy P. Henning, Vernon Hills; Eric B. Shain, Glencoe; Douglas F. Young, Grayslake; Michael G. Lowery, Wildwood, all of IL (US); Thomas G. Schapira, Bristol, WI (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/546,948

(22) Filed: Apr. 11, 2000

Related U.S. Application Data

(60) Division of application No. 08/982,323, filed on Dec. 2, 1997, now Pat. No. 6,071,251, and a continuation-in-part of application No. 08/759,698, filed on Dec. 6, 1996, now Pat. No. 6,063,039.
(60) Provisional application No. 60/036,395, filed on Jan. 24, 1997.

(51) Int. Cl.[7] .................................................... A61B 5/00
(52) U.S. Cl. ................................................................ 600/584
(58) Field of Search ..................................... 600/573, 576, 600/578, 583, 584; 606/181

(56) References Cited

U.S. PATENT DOCUMENTS 3,419,000 * 12/1968 Phillips ................................ 600/584

(List continued on next page.)

FOREIGN PATENT DOCUMENTS 2803345   6/1979 (DE) .

(List continued on next page.)

OTHER PUBLICATIONS

A.E.G. Cass, et al., "Ferrocene–Mediated Enzyme Electrode for Amperometric Determination of Glucose ", Anal. Chem., vol. 56, ( 1984), pp. 667–671.

Primary Examiner—Cary O'Connor
Assistant Examiner—Pamela Wingood
(74) Attorney, Agent, or Firm—David L. Weinstein

(57) ABSTRACT

Method and apparatus for obtaining a sample of blood from a patient for subsequent diagnostic tests, e.g., glucose monitoring. In one aspect of the invention, the method comprises the steps of:

(a) forming an unobstructed opening in the area of the skin from which the sample of blood is to be extracted; and (b) extracting the sample of blood from the unobstructed opening in the skin, with the aid of a vacuum and a stretching of the skin.

In another aspect of the invention, an apparatus for carrying out the method described previously is provided. The apparatus comprises:

(a) a device for forming an unobstructed opening in an area of skin from which said sample is to be extracted, preferably a lancing assembly; and (b) a vacuum pump.
Preferably, the apparatus also includes a housing.

In another aspect of this invention, an article is provided for an article capable of both collecting blood and detecting an analyte in that blood is provided. The article, which contains an appropriate detection element for determining the amount of analyte in the blood, can be used in conjunction with a meter that measures the signal generated by the detection element of the article. In one embodiment, the article is a multiple-layer element comprising:

(a) a layer capable of receiving blood and transporting the blood received by means of chemically aided wicking;

(b) a layer capable of detecting the presence of analyte or measuring the amount of analyte in blood; and (c) a layer that can be placed in contact with a meter, the meter-contactable layer overlying the blood-transporting layer, said layer (a) capable of transporting blood to said layer (b).

9 Claims, 12 Drawing Sheets

U.S. PATENT DOCUMENTS

| | | | |
|---|---|---|---|
| 4,233,029 | * 11/1980 | Columbus | 23/230 |
| 4,545,382 | 10/1985 | Higgins et al. . | |
| 4,627,445 | 12/1986 | Garcia et al. . | |
| 4,711,245 | 12/1987 | Higgins et al. . | |
| 4,851,210 | * 7/1989 | Hewett | 424/11 |
| 4,929,545 | 5/1990 | Freitag . | |
| 4,935,346 | 6/1990 | Phillips et al. . | |
| 5,037,431 | 8/1991 | Summers et al. . | |
| 5,120,420 | 6/1992 | Nankai et al. . | |
| 5,161,532 | 11/1992 | Joseph . | |
| 5,192,415 | 3/1993 | Yoshioka et al. . | |
| 5,243,516 | 9/1993 | White . | |
| 5,250,439 | * 10/1993 | Musho et al. | 435/25 |
| 5,264,103 | 11/1993 | Yoshioka et al. . | |
| 5,266,179 | 11/1993 | Nankai et al. . | |
| 5,320,607 | 6/1994 | Ishibashi . | |
| 5,352,351 | 10/1994 | White et al. . | |
| 5,354,447 | 10/1994 | Uenoyama et al. . | |
| 5,405,511 | 4/1995 | White et al. . | |
| 5,413,690 | 5/1995 | Kost et al. . | |
| 5,443,080 | * 8/1995 | D'Angelo et al. | 600/584 |
| 5,509,410 | 4/1996 | Hill et al. . | |
| 5,628,890 | 5/1997 | Carter et al. . | |
| 5,682,884 | 11/1997 | Hill et al. . | |

FOREIGN PATENT DOCUMENTS

| | | |
|---|---|---|
| 3708031 | 11/1987 | (DE) . |
| 0021798 | 1/1981 | (EP) . |
| 0127958 | 12/1984 | (EP) . |
| 0212906 | 3/1987 | (EP) . |
| 0230472 | 8/1987 | (EP) . |
| 0254203 | 1/1988 | (EP) . |
| 0351892 | 1/1990 | (EP) . |
| 0371503 | 6/1990 | (EP) . |
| 0429076 | 5/1991 | (EP) . |
| 0449525 | 10/1991 | (EP) . |
| 0451981 | 10/1991 | (EP) . |
| 0520296 | 12/1992 | (EP) . |
| 0575952 | 12/1993 | (EP) . |
| 0590661 | 4/1994 | (EP) . |
| 0636880 | 2/1995 | (EP) . |
| 0671146 | 9/1995 | (EP) . |
| 0732590 | 9/1996 | (EP) . |
| 0797951 | 10/1997 | (EP) . |
| 2222251 | 2/1990 | (GB) . |
| 9109139 | 6/1991 | (WO) . |
| 9202175 | 2/1992 | (WO) . |
| 9215863 | 9/1992 | (WO) . |
| 9303673 | 3/1993 | (WO) . |
| 9409713 | 5/1994 | (WO) . |
| 9637148 | 11/1996 | (WO) . |
| 9742882 | 11/1997 | (WO) . |

* cited by examiner

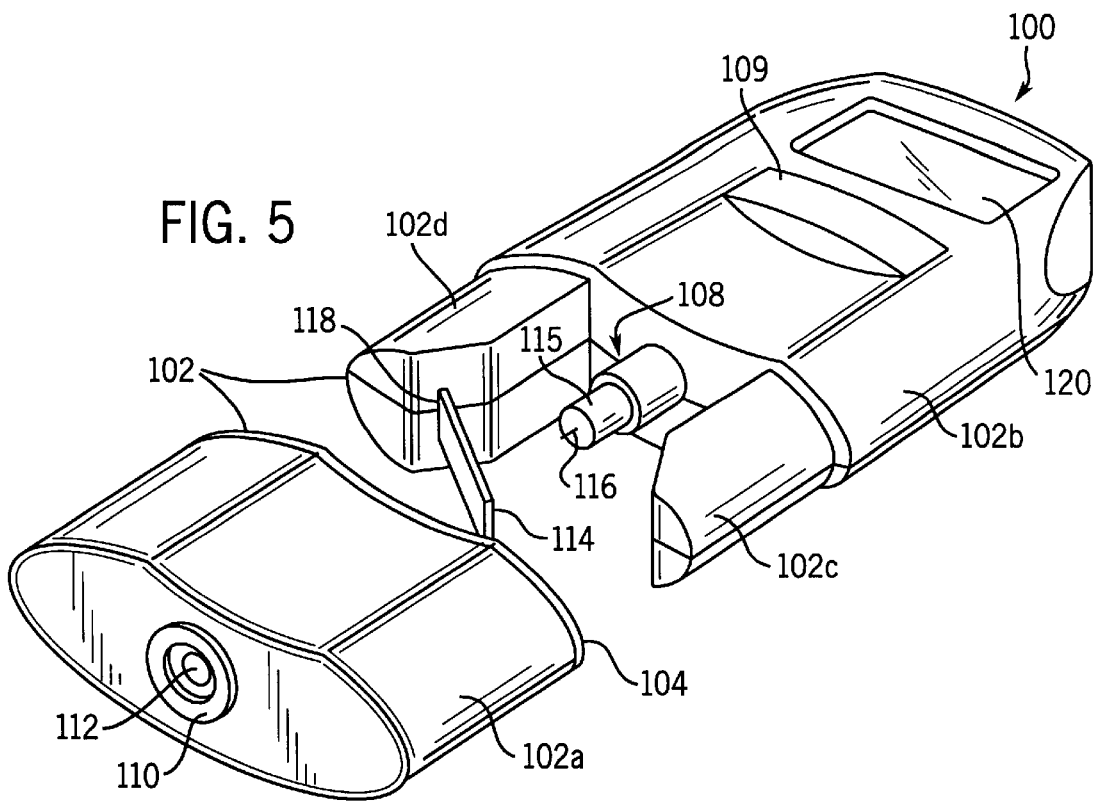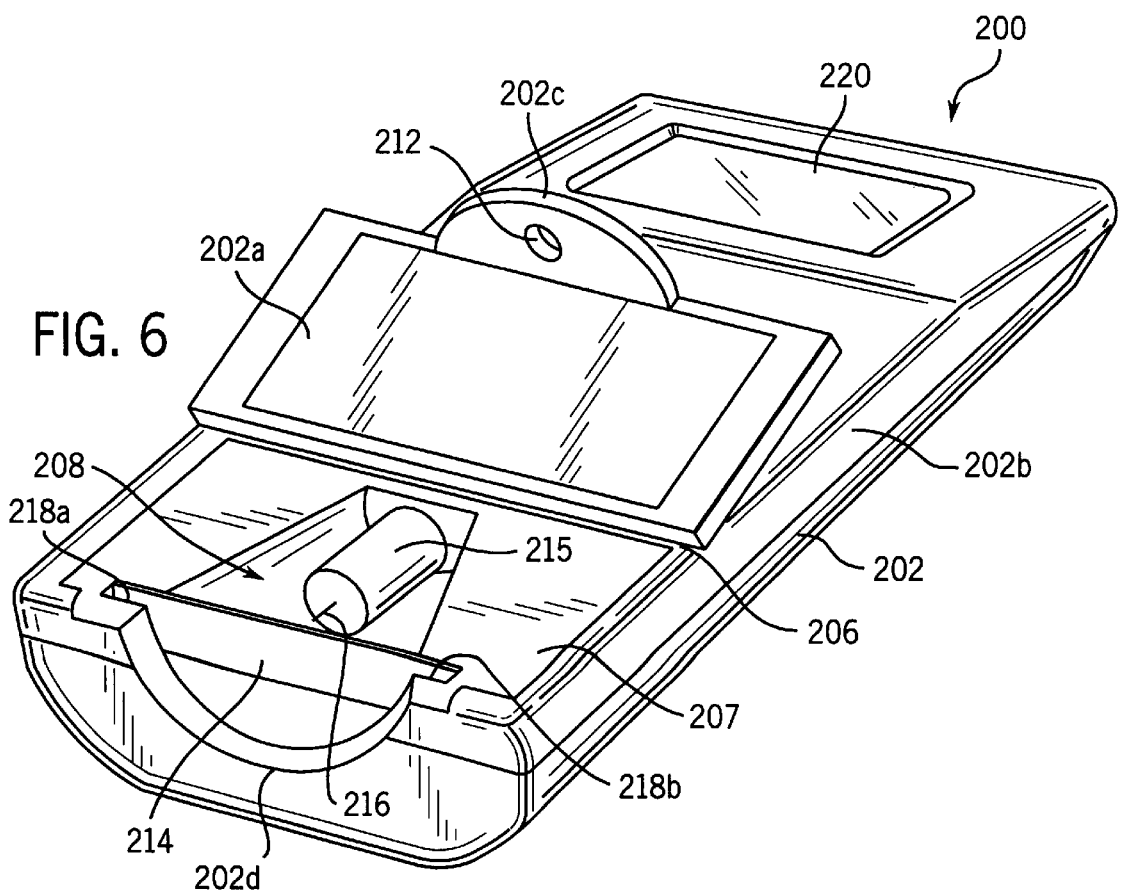

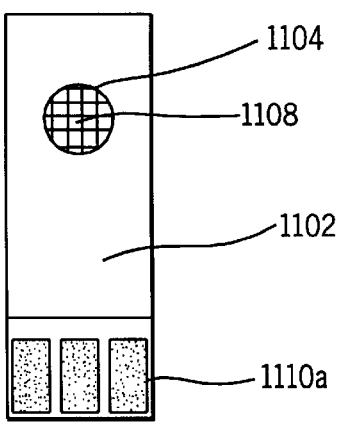
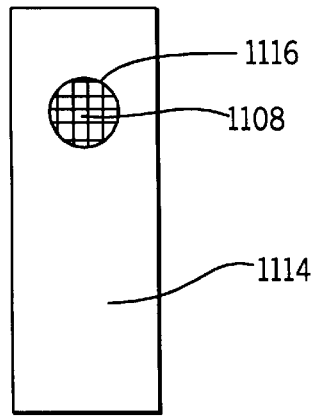
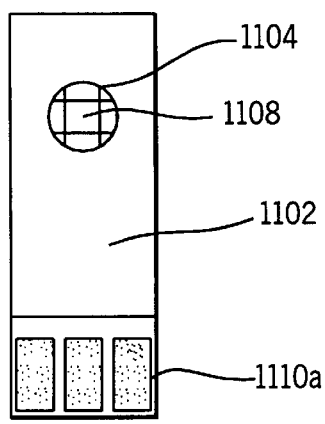
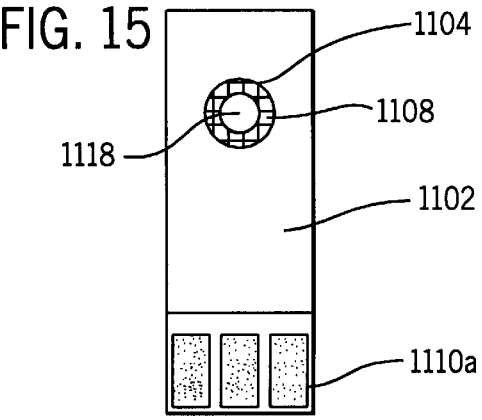
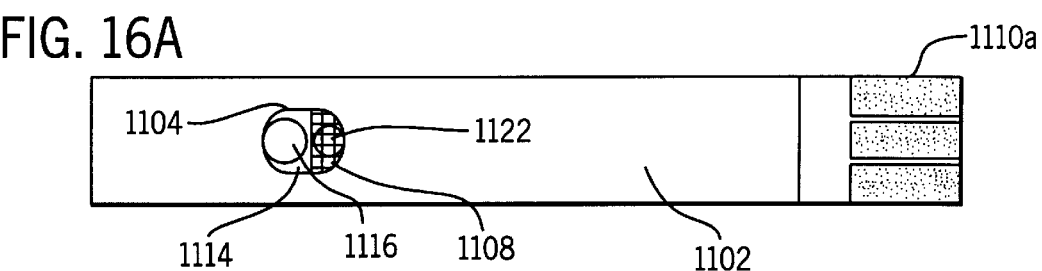
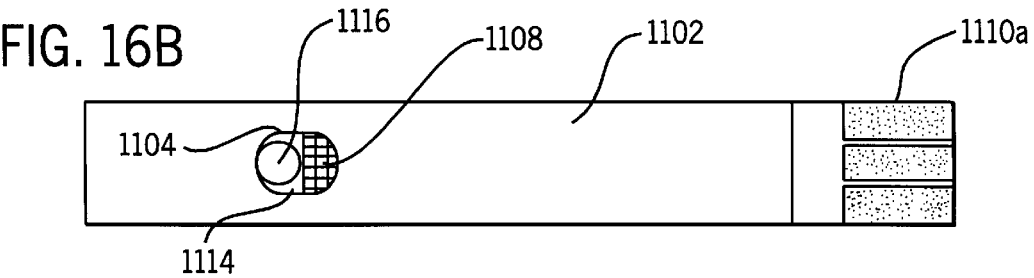

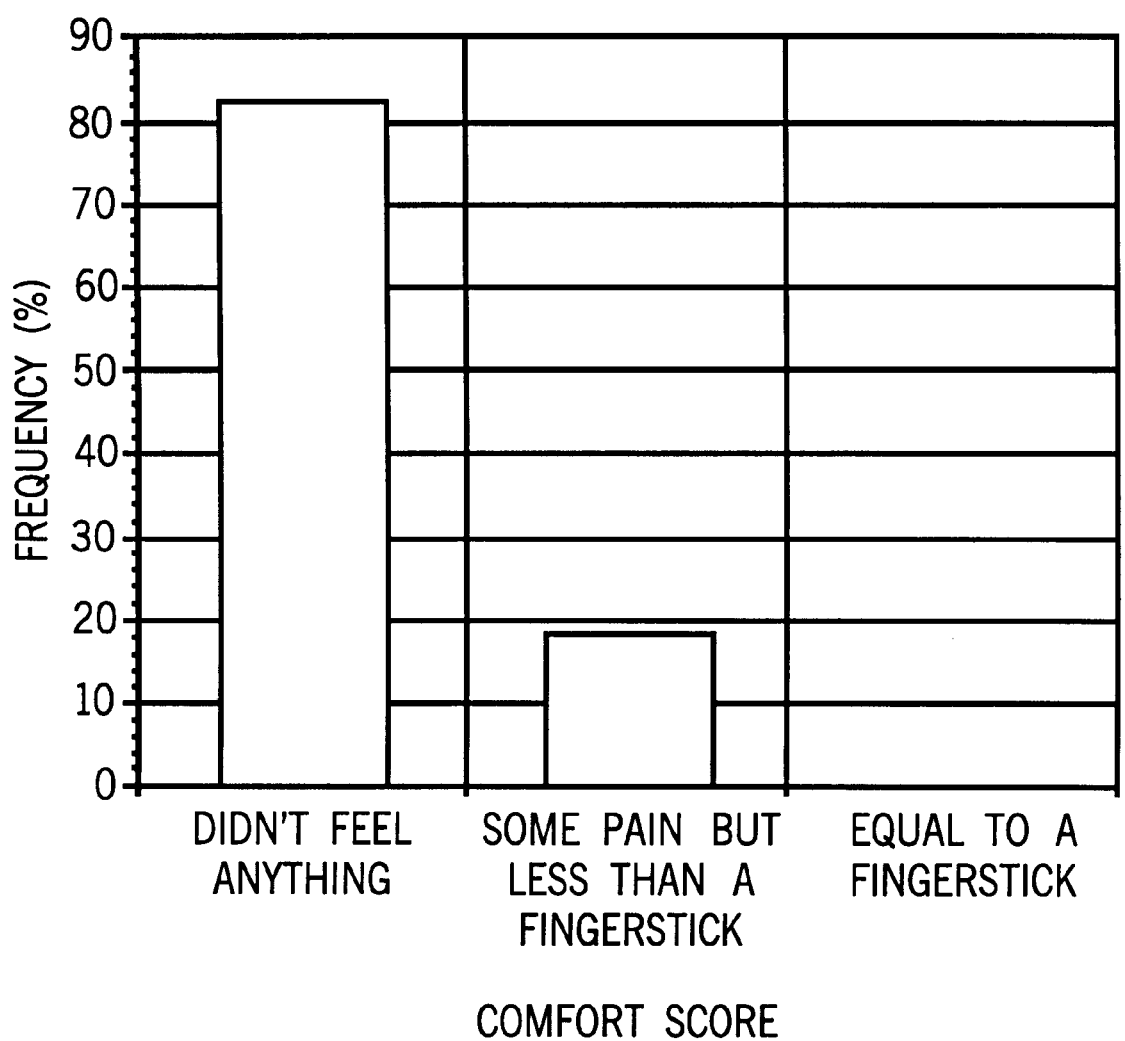

METHOD AND APPARATUS FOR OBTAINING BLOOD FOR DIAGNOSTIC TESTS

This application is a Division of application Ser. No. 08/982,323 filed Dec. 2, 1997, U.S. Pat. No. 6,071,251 and a continuation-in-part of U.S. application Ser. No. 08/759,698, filed Dec. 6, 1996, now U.S. Pat. No. 6,063,039 and a continuation-in-part of U.S. Provisional application Ser. No. 60/036,395, filed Jan. 24, 1997.

CROSS REFERENCES TO COPENDING APPLICATIONS

This application relates to three patent applications, METHOD AND APPARATUS FOR OBTAINING BLOOD FOR DIAGNOSTIC TESTS, Attorney's Docket No. 6005.US.P1, METHOD AND APPARATUS FOR OBTAINING BLOOD FOR DIAGNOSTIC TESTS, Attorney's Docket No. 6005.US.P3, METHOD AND APPARATUS FOR OBTAINING BLOOD FOR DIAGNOSTIC TESTS, Attorney's Docket No. 6005.US.P4, filed on even-date herewith. The specifications, drawings, and claims of these applications are incorporated herein by reference. All of the foregoing applications are commonly owned by the assignee of this invention.

BACKGROUND OF THE INVENTION

1. Field of the Invention

This invention relates to a method and apparatus for obtaining samples of blood for diagnostic purposes.

2. Discussion of the Art

The prevalence of diabetes has been increasing markedly in the world. At this time, diagnosed diabetics represented about 3% of the population of the United States. It is believed that the total actual number of diabetics in the United States is over 16,000,000. Diabetes can lead to numerous complications, such as, for example, retinopathy, nephropathy, and neuropathy.

The most important factor for reducing diabetes-associated complications is the maintenance of an appropriate level of glucose in the blood stream. The maintenance of the appropriate level of glucose in the blood stream may prevent and even reverse many of the effects of diabetes.

Glucose monitoring devices of the prior art have operated on the principle of taking blood from an individual by a variety of methods, such as by needle or lancet. An individual then coats a paper strip carrying chemistry with the blood, and finally insert the blood-coated strip into a blood glucose meter for measurement of glucose concentration by determination of change in reflectance.

The medical apparatus of the prior art for monitoring the level of glucose in the blood stream required that an individual have separately available a needle or lancet for extracting blood from the individual, strips carrying blood chemistry for creating a chemical reaction with respect to the glucose in the blood stream and changing color, and a blood glucose meter for reading the change in color indicating the level of glucose in the blood stream. The level of blood glucose, when measured by a glucose meter, is read from a strip carrying the blood chemistry through the well-known process of reading reflectometers for glucose oxidation.

Generally lancets comprise a blade and a pressable end opposed thereto, with the blade having an acute end capable of being thrust into skin of a human. By striking the pressable portion, the acute end of the blade will pierce the skin, for example, of the finger. The finger lancet is primarily used to obtain small volumes of blood, i.e., less than 1 mL. Diabetics use the finger lancet to obtain volumes of blood less than 25 $\mu$L for analysis for glucose. A small amount of blood for the blood test will ooze out of the skin. There are many small blood vessels in each finger so that a finger can be squeezed to cause a larger drop of blood to ooze. The finger is one of the most sensitive parts of the body; accordingly, the finger lancet leads to even more pain than what would be experienced by extracting blood via lancet at a different body site. The finger lancet presents another problem because of the limited area available on the fingers for lancing. Because it is recommended that diabetics monitor their blood glucose levels four to six times per day, the limited area on the fingers calls for repeated lancing of areas that are already sore. Because fingers are sensitive to pain, it is a recent tendency that the arm is subjected to blood sampling. See, for example, U.S. Pat. No. 4,653,513. The device of U.S. Pat. No. 4,653,513 comprises a cylindrical housing and a lancet support, which has a gasket or flexible portion slidably accommodated in the housing. Springs will retract the lancet support to thereby reduce air pressure in the housing so that it sucks a blood sample, automatically and immediately after a lancet pierces the skin. See also U.S. Pat. No. 5,320,607, which discloses a device comprising a sealed vacuum chamber in a state of preexisting reduced pressure, a support member for the sealed vacuum chamber, the support member defining a suction portion adjacent the sealed vacuum chamber, the suction portion, in cooperation with the sealed vacuum chamber, exposing an area of the skin of a patient to a reduced pressure state when the device is actuated, and means arranged within the suction portion for slightly rupturing a portion of the area of skin of the patient exposed to the reduced pressure state.

Because the blood volume requirements for a standard glucose test strip is typically 3 $\mu$L or more, an area of the body that can generate that much blood from a lancet wound must be used. It is believed, however, that improvements in glucose test strip technology will reduce the volume of blood needed to 1 to 3 $\mu$L. Because the finger is well supplied with blood and the amount of blood can be increased by squeezing the finger after lancing, the finger is the currently preferred body site for lancing, even though lancing of the finger is painful.

A less painful technique for obtaining body fluids could be found if a reliable method were found for lancing a body part that is less sensitive to pain than the finger and obtaining a useful amount of blood from that body part. A body part such as the forearm is much less sensitive to pain than the finger, but the amount of blood resulting from the lancing procedure is generally of an inadequate volume for use with current detection technology. Ways of increasing blood flow to the finger are common knowledge. The recommendation is made to diabetics to run their finger under hot water prior to lancing to improve the blood flow in the finger and the amount of blood collected from the finger. Running hot water over a body part to improve blood flow is impractical for areas such as the forearm or thigh. The availability of hot water is also a concern.

It would be desirable to develop a technique and apparatus for obtaining blood for diagnostic purposes in a painless, reliable manner.

The blood obtained from a lancet stick has typically been manually transferred by the user from the finger to the detector. However, such manual transfer is difficult for users who exhibit poor dexterity, poor eyesight, or who are prone to shaking (hypoglycemic diabetics). Manual transfer can also lead to errors in the glucose determination if too much or too little blood is transferred.

SUMMARY OF THE INVENTION

This invention provides a method and apparatus for extracting a sample of blood from a patient for subsequent diagnostic tests, e.g., glucose monitoring. In one aspect of the invention, the method comprises the steps of:

(a) forming an unobstructed opening in the area of the skin from which the sample of blood is to be extracted; and (b) extracting the sample of blood from the unobstructed opening in the skin, with the aid of vacuum and stretching of the skin.

In a preferred embodiment of the method, step (a) is preceded by the step of increasing the availability of blood in the portion of the skin from which the sample is to be extracted. In this preferred embodiment, the availability of blood in the portion of the skin from which the sample is to be extracted can be increased by means of a vacuum, which is applied to the surface of the skin in the vicinity of the opening prior to forming the opening in the skin. The vacuum causes the portion of the skin in the vicinity of the blood extraction site to become engorged with blood. The vacuum also causes the portion of the skin in the vicinity of the blood extraction site to become stretched. An opening in this stretched portion of skin can be formed with a cutting or puncturing device, e.g., a lancet, or other device capable of forming an opening in the skin, e.g., a laser or a fluid jet. If a cutting or puncturing device is used to form the opening, it must be retracted from the opening prior to the step of extracting the sample of blood from the opening. This retraction will allow the unrestricted flow of blood through the opening. After the opening is formed, a vacuum is used to aid in extracting the sample of blood from the opening in the skin. The sample can be analyzed from the drops of blood that collect on the surface of the skin at the site of the opening by applying the blood directly to a glucose detector. It is preferred, however, that the sample be collected in such a manner, e.g., via a capillary tube, that it can be analyzed by conventional diagnostic devices, such as, for example, a biosensor. In another preferred embodiment, the sample can be collected in a collection zone that is integrated with a conventional diagnostic device, e.g., a biosensor.

In an alternative of the aforementioned preferred embodiment, the availability of blood in the area of the skin from which the sample is to be extracted can be increased by means of applying thermal energy to that area of skin. The thermal energy causes the blood in that area of the skin to flow more rapidly, thereby allowing more blood to be collected per given unit of time. In this alternative embodiment, steps (a) and (b) can be carried out in the same manner as they were carried out in the aforementioned preferred embodiment.

In another aspect of the invention, an apparatus for collecting a sample of body fluid for analysis in a diagnostic test, e.g., blood, is provided. In a preferred embodiment, the apparatus comprises:

(a) a housing;

(b) a device for forming an unobstructed opening in an area of skin from which said sample is to be extracted, preferably a lancing assembly; and (c) a vacuum pump.

It is also possible to dispense with the housing. However, the housing is preferred for the convenience of the patient and the protection of the components.

The vacuum pump requires a source of power. If the apparatus includes a housing, the source of power can be disposed within the housing. Alternatively, the source of power can be external to the housing.

The preferred device for forming an unobstructed opening in the area of the skin from which the sample of blood is to be extracted is a lancing assembly, which comprises a lancet for forming an opening in the skin. Alternatively, the unobstructed opening in the skin can be formed by a laser or a fluid jet.

The vacuum pump can serve the dual purposes of (1) stretching the skin and (2) enhancing the extraction of the sample of blood from the unobstructed opening in the skin. Preferably, the vacuum pump can serve the triple purposes of (1) stretching the skin, (2) increasing the availability of blood to the area of the skin from which the sample is to be extracted, and (3) enhancing the extraction of the sample of blood from the unobstructed opening in the skin. Preferably, the housing further contains electronics having programmed instructions to switch the vacuum pump on and off to maintain the desired level of vacuum.

The apparatus preferably contains valves, such as, for example, solenoid valves, for triggering the lancet of the lancing assembly and releasing the vacuum at the conclusion of the blood extraction procedure. The apparatus can optionally contain a heating element to increase the availability of blood to the area of the skin from which the sample is to be extracted. The apparatus can also contain a glucose detector integrated with the apparatus, e.g., a biosensor, to analyze the sample of blood collected by the apparatus.

In another aspect, this invention provides an article capable of both collecting blood and detecting an analyte in that blood. Preferably, the article is also capable of measuring the amount of analyte in the blood. The article, which contains an appropriate detection element for determining the amount of analyte in the blood, can be used in conjunction with a meter that measures the signal generated by the detection element of the article.

In one embodiment, the article is a multiple-layer element comprising:

(a) a layer capable of receiving blood and transporting the blood received by means of chemically aided wicking;

(b) a layer capable of detecting the presence of analyte or measuring the amount of analyte in blood; and (c) a layer that can be placed in contact with a meter, the meter-contactable layer overlying the blood-transporting layer, said layer (a) capable of transporting blood to said layer (b).

In a preferred embodiment, the article is a multiple-layer element comprising:

(a) a covering layer having an opening therein;

(b) a layer, overlying the covering layer, capable of receiving blood through the opening in the covering layer and transporting blood by means of chemically aided wicking;

(c) a layer that can be placed in contact with a meter, the meter-contactable layer overlying the blood-transporting layer; and (d) a layer capable of detecting the presence of analyte or measuring the amount of analyte in blood, which layer is disposed between the covering layer and the meter-contactable layer and is capable of receiving blood from the blood-transporting layer.

An optional overcoat layer can be interposed between the covering layer and the meter-contactable layer to restrict the flow of blood in the blood-transporting layer.

In another embodiment, the blood-transporting layer can be eliminated. In this embodiment, the meter-contactable layer and the covering layer utilize capillary- action to tranport the blood by capillary flow to the detecting layer.

In order to use the multiple-layer element, a vacuum is used to stretch the skin and draw the skin into contact with the covering layer of the element. The vacuum is applied for a sufficient period of time to cause blood to pool in the stretched skin. Then an unobstructed opening is formed in the skin, typically by a retractable lancet. Blood emerges from the unobstructed opening in the skin and enters the blood-transporting layer. The opening in the covering layer renders it possible for the blood emerging from the unobstructed opening in the skin to enter the blood-transporting layer. The blood then moves along or through the blood-transporting layer to the detecting layer. Preferably, the detecting layer comprises an electrochemical sensor or an optical sensor. A chemical reaction occurs at the surface of the detecting layer. The result of the chemical reaction can then be read by a meter.

The multiple-layer element integrates the the blood-transporting layer, the meter-contactable layer, the detecting layer, and, when employed, the covering layer into one element. This integrated element can be made at a low enough cost to be disposable. The multiple-layer element makes it possible to obtain accurate results with small samples of blood, because no blood is spilled during transfer of the blood to the detecting layer.

The multiple-layer element can wick up blood that emerges from the unobstructed opening formed in the skin and direct the blood to the detecting layer of the multiple-layer element where a diagnostic test, such as, for example, measurement of concentration of analyte, e.g., glucose, in blood, is made. Transfer of the blood by manual means is not required. The detecting layer can also be used for the additional purpose of sending a signal to the blood collecting apparatus of this invention to release the vacuum when sufficient blood has been drawn into the multiple-layer element to provide a reliable diagnostic test. The multiple-layer element can also be used as a barrier to stop a lancet assembly to control the depth of the unobstructed opening formed in the skin.

The method and apparatus of this invention provide several advantages over the methods and apparatus of the prior art. First, a sufficient amount of blood can be extracted from parts of the body, other than the finger, for conducting glucose monitoring tests. Second, by rendering other parts of the body suitable for extracting blood, the use of a painful finger lance can be avoided. Third, by increasing the availability of blood at the site where the blood is to be extracted, the period of time required for extracting the sample can be reduced. Because of these advantages, the diabetic patient is more likely to monitor glucose levels in the blood at the intervals prescribed by his doctor.

BRIEF DESCRIPTION OF THE DRAWINGS

FIG. 2 also illustrates the spatial relationship between the nosepiece of lancing assembly and a glucose detector, e.g., a biosensor.

FIG. 5 is a perspective view of an embodiment of the apparatus of this invention. In this figure, the housing of the apparatus is open.

FIG. 6 is a perspective view of an embodiment of the apparatus of this invention. In this figure, the housing of the apparatus is open.

FIG. 11B is a peeled-apart exploded perspective view.

FIG. 12 is a top plan view of one embodiment of a multiple-layer element wherein the blood-transporting layer is a fine mesh.

FIG. 13 is a bottom plan view of the embodiment of the multiple-layer element of FIG. 12.

FIG. 14 is a top plan view of one embodiment of a multiple-layer element wherein the blood-transporting layer is a coarse mesh.

FIG. 15 is a top plan view of one embodiment of a multiple-layer element wherein the blood-transporting layer is a fine mesh having an opening formed therein.

FIG. 16A is a top plan view of one embodiment of a multiple-layer element wherein the blood-transporting layer is a fine mesh. The meter-contactable layer has two openings punched therein.

FIG. 16B is a top plan view of one embodiment of a multiple-layer element wherein the blood-transporting layer is a fine mesh. The meter-contactable layer has a single opening therein.

FIG. 21 is a graph illustrating pain of lancet of forearm compared to pain of lancet of finger.

DETAILED DESCRIPTION

Figure 1:
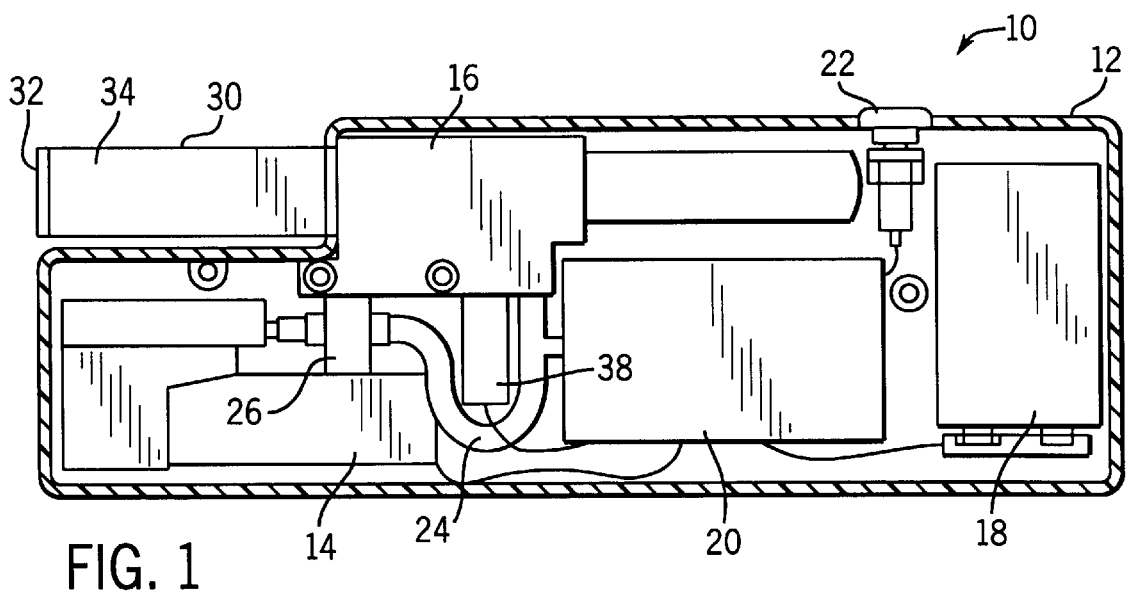
FIG. 1 is a plan view of the components of a preferred embodiment of the apparatus of this invention. In this Figure, the cover of the housing is removed.

The embodiments of this invention require the following steps to carry out the function of obtaining a sample of blood for carrying out a diagnostic test, e.g., glucose monitoring:

(a) forming an unobstructed opening in the area of the skin from which the sample of blood is to be extracted; and (b) extracting the sample of blood from the unobstructed opening in the skin, with the aid of a vacuum and a stretching of the skin.

The step of forming an unobstructed opening in the area of the skin from which the sample of blood is to be extracted is carried out by a piercing device or some other type of device capable of forming an unobstructed opening in the skin. Piercing devices suitable for this invention include, but are not limited to, mechanical lancing assemblies. Other type of device capable of forming an unobstructed opening in the skin include, but are not limited to, lasers and fluid jets. Other types of devices capable of forming an unobstructed opening in the skin can be used, and this disclosure should not be construed so as to be limited to the devices listed. Mechanical lancing assemblies are well-known in the art. These assemblies comprise include standard steel lancets, serrated devices, and multiple tip devices. The lancets can be made from metal or plastic. Multiple tip devices provide redundancy, which can reduce the number of failures and increase the volume of blood extracted.

Lasers suitable for forming an unobstructed opening in the skin to draw blood are also well-known in the art. See for example, U.S. Pat. Nos. 4,775,361, 5,165,418, 5,374,556, International Publication Number WO 94/09713, and Lane et al. (1984) IBM Research Report—"Ultraviolet-Laser Ablation of Skin", all of which are incorporated herein by reference. Lasers that are suitable for forming an unobstructed opening in the skin the skin include Er:YAG, Nd:YAG, and semiconductor lasers.

Fluid jets suitable for forming an unobstructed opening in the skin employ a high pressure jet of fluid, preferably a saline solution, to penetrate the skin.

Regardless of what type of device is utilized to form an unobstructed opening in the skin, the opening formed by the device must be unobstructed. As used herein, the term "unobstructed" means free from clogging, hampering, blocking, or closing up by an obstacle. More specifically, the expressions "unobstructed opening in the area of the skin from which the sample is to be extracted", "unobstructed opening in the skin", and the like are intended to mean that the portion of the opening below the surface of the skin is free from any foreign object that would clog, hamper, block, or close up the opening, such as, for example, a needle of any type. For example, if a lancet is used to form the opening, it must be retracted from the opening prior to the commencement of the extraction of blood. Because lasers and fluid jets do not require contact with the skin to form openings in the skin, these types of devices typically provide unobstructed openings. However, these expressions are not intended to include foreign objects at the surface of the skin or above the surface of the skin, such as, for example, a glucose monitor. This feature, i.e., the unobstructed opening, can be contrasted with the opening used in the method and apparatus described in U.S. Pat. No. 5,320,607, in which the piercing and cutting means remains in the skin during the duration of the period of blood extraction. By leaving the opening unobstructed, blood can be extracted much more rapidly from the opening than it would be extracted if the piercing and cutting means were allowed to remain in the opening. In addition, the requirement of an unobstructed opening exposes the body to a foreign object either not at all or for only a very short period of time, which is welcomed by the patient.

The step of extracting the sample of blood from the opening in the skin is carried out by a combination of extraction enhancing elements. Extraction enhancing elements suitable for use in this invention include, but are not limited to, vacuum, skin stretching elements, and heating elements. It has been discovered that when these elements are used in combination, the volume of blood extracted is greatly increased, particularly when a vacuum is applied in combination with skin stretching. In this combination, the vacuum not only causes the blood to be rapidly removed from the unobstructed opening by suction, it also causes a portion of the skin in the vicinity of the opening to be stretched. Stretching of the skin can be effected by other means, such as mechanical means or adhesives. Mechanical means include devices for pinching or pulling the skin; adhesives bring about stretching of the skin by means of pulling. It is preferred to use a vacuum to effect stretching of the skin. Like a vacuum, a heating element operates more effectively in combination with other techniques, e.g., stretching of the skin.

In the preferred embodiment of this invention, step (a), the step of forming the unobstructed opening, is preceded by the step of increasing the availability of blood at the area of the skin from which the sample is to be extracted. The availability of blood at a given area of the skin can be increased by at least two methods. In one method, a vacuum can be used to cause blood flowing through blood vessels to pool in the area of the skin where the vacuum is applied. In another method, heat can be used to cause blood flowing through blood vessels to flow more rapidly in the area of the skin where heat is applied, thereby allowing a greater quantity of blood to be extracted from the blood extraction site per unit of time. Although the step of increasing the availability of blood in the vicinity of the blood extraction site is not required, the employment of this step can result in a greater volume of blood extracted. Elements for increasing the availability of blood at a blood extraction site that are suitable for use in this invention include, but are not limited to, vacuum, localized heating element, skin stretching element, and chemicals. As stated previously, applying a vacuum to the area of the skin from which blood is to be extracted can increase blood availability under and within the skin at the application site. The vacuum can also be used to stretch the skin upwardly into a chamber, thereby increasing pooling of blood under and within the skin. This combination of vacuum and skin stretching can be an extension of the combination used to extract blood from the opening in the skin, as previously described. It is well-known that heat can increase perfusion on the large scale of a limb or a finger. Chemical means, such as histamine, can be used to cause a physiological response to increase perfusion under and within the skin.

In the preferred embodiments of the invention, the extracted blood is also collected. The step of collecting the sample of blood can be carried out in a variety of ways. For example, the blood can be collected in capillary tubes or absorbent paper. Alternatively, the blood can be allowed to remain in the lancet assembly, from which it can used directly in a diagnostic test. Most preferably, the sample of blood is collected on the application zone of a glucose detector, from where it can be used directly to provide an indication of the concentration of glucose in the blood. Regardless of the manner in which the blood sample is collected, the sample can be analyzed at a time later than the time of collection or at a location remote from the location of collection or both.

A preferred embodiment of the invention will now be described in detail. Blood extraction device 10 comprises a housing 12. Disposed within the housing 12 are a vacuum pump 14, a lancing assembly 16, a battery 18, and electronics 20. A switch 22 is provided to activate electronics 20.

The housing 12 is preferably made from a plastic material. It is preferably of sufficient size to contain all of the components that are required for forming an unobstructed opening in the area of the skin from which the sample of blood is to be extracted, extracting the sample of blood from the unobstructed opening in the skin, preferably with the aid of a vacuum and a stretching of the skin, and collecting the extracted sample in an amount sufficient to carry out a diagnostic test. Methods of preparing the housing 12 are well-known to one of ordinary skill in the art. As stated previously, the housing 12 is not required, but is preferred for the convenience of the patient and the protection of the components.

The vacuum pump 14 must be capable of providing a vacuum that will provide sufficient suction to stretch the portion of the skin in the region from which the sample of blood is to be extracted. Typically, the portion of stretched skin is raised a distance of 1 to 10 mm, preferably 3 to 5 mm, from the plane of the body part of which it is a portion. As the suction provided by the vacuum pump 14 is stretching the appropriate portion of skin, the suction provided by the vacuum pump 14 also causes the stretched portion to become engorged with blood. The level of suction provided must be sufficient to cause a relatively large volume of blood to become engorged at the point that the vacuum is applied. The vacuum pump 14 must also be capable of providing sufficient suction to extract blood from the opening in the skin at a rate sufficient to extract at least 1 $\mu$L of blood within a period of five minutes. A vacuum pump 14 that is suitable for the device of this invention can be a diaphragm pump, a piston pump, a rotary vane pump, or any other pump that will perform the required functions set forth previously. Typically, the vacuum pump 14 employs a self-contained permanent magnet DC motor. Vacuum pumps that are suitable for this invention are well-known to those of ordinary skill in the art and are commercially available. A vacuum pump suitable for use in the present invention is available from T-Squared Manufacturing Company, Nutley, N.J., and has the part number T2-03.08.004.

The vacuum pump 14 is preferably capable of providing a pressure of down to about −14.7 psig, and is more preferably operated at from about −3.0 psig to about −10.0 psig. The area of the skin subjected to vacuum preferably ranges up to about 50 cm$^2$, more preferably from about 0.1 to about 5.0 cm$^2$. The period of vacuum application prior to forming the opening in the skin, i.e., for increasing the availability of blood to the application site, preferably ranges up to about 5 minutes, preferably from about 1 to about 15 seconds. The period of vacuum application subsequent to forming the opening in the skin, i.e., for aiding in the extraction of blood from the unobstructed opening, preferably ranges up to about 5 minutes, preferably from about 1 to about 60 seconds. The vacuum provided by the vacuum pump 14 can be continuous or pulsed. A continuous vacuum is preferred for the reason that it requires fewer components than does a pulsed vacuum. It is preferred that the vacuum applied not cause irreversible damage to the skin. It is preferred that the vacuum applied not produce bruises and discolorations of the skin that persist for several days. It is also preferred that the level of vacuum applied and duration of application of vacuum not be so excessive that it causes the dermis to separate from the epidermis, which results in the formation of a blister filled with fluid.

The vacuum pump feature offers significant advantages over the method and apparatus described in U.S. Pat. No. 5,320,607, in which a sealed vacuum chamber in a state of preexisting reduced pressure is used. The use of a vacuum pump provides the user with greater control of blood extraction conditions than does a sealed vacuum chamber in a state of preexisting reduced pressure. For example, if the vacuum is insufficient, energy can be provided to the vacuum pump to bring about a higher level of vacuum, thereby providing greater suction.

The lancing assembly 16 comprises at least one lancet. Standard lancets can be used in the lancing assembly of this invention. Narrow gauge (28 to 30 gauge) lancets are preferred. Lancets suitable for this invention can be made from metal or plastic. Lancets suitable for this invention can have single points or multiple points. The depth of penetration of the lancet preferably ranges from about 0.4 to about 2.5 mm, more preferably from about 0.4 to about 1.6 mm. The length of the lancet or lancets preferably ranges from about 1 mm to about 5 mm. The lancing assembly is preferably located so that the user can easily replace used lancets. The lancet of the lancing assembly 16 can be cocked manually or automatically, e.g., by means of a vacuum-actuated piston or diaphragm. The lancet of the lancing assembly 16 can be triggered by manually or automatically, e.g., by means of a vacuum-actuated piston or diaphragm.

Lancing assemblies are well-known in the art. Representative examples of lancing assemblies suitable for this invention are described in U.S. Pat. Nos. Re. 32,922, 4,203, 446, 4,990,154, and 5,487,748, all of which are incorporated herein by reference. A particularly suitable lancing assembly for this invention is described in U.S. Pat. No. Re. 32,922. However, any lancing assembly selected should operate in conjunction with the other features of the apparatus of this invention. For example, if a vacuum is employed, the lancing assembly must be designed so that a vacuum can be formed and drawn through the assembly. The lancing assembly can be designed to allow automatic cocking and automatic triggering of the lancet.

The vacuum pump 14 is connected to the lancing assembly 16 by an evacuation tube 24. The air that is evacuated from the lancing assembly 16 by the vacuum pump 14 is removed via the evacuation tube 24. The evacuation tube 24 is typically made from a polymeric material. A check valve 26 is placed between the vacuum pump 14 and the lancing assembly 16 at a point in the evacuation tube 24 to prevent air removed from the lancing assembly 16 by the vacuum pump 14 from flowing back to the lancing assembly 16 and adversely affecting the vacuum.

A source of power for the vacuum pump 14 can be disposed within the housing 12. A source of power suitable for the device of this invention is a battery 18. Alternatively, an external source of power can be used to operate the vacuum pump 14. The power source is actuated by the electronics 20, which, in turn, is actuated by the switch 22.

The electronics 20 may incorporate a microprocessor or microcontroller. The function of the electronics 20 is to switch power on and off to operate the various components in the apparatus. These components include, but are not limited to, the vacuum pump 14. The electronics 20 can also be use to switch power on and off to operate components in alternative embodiments, e.g., heating elements, lancets, indicating devices, and valves. Electronics suitable for this invention is the "TATTLETALE MODEL 5F" controller/data logger, commercially available from Onset Computer Corporation, 536 MacArthur Blvd. P. O. Box 3450, Pocasset, Mass. 02559-3450. Auxiliary electronic devices, such as power transistors, pressure monitors, and OP-Amps (operational amplifiers), may also be required in order to provide an interface between the controller and the operational components. All electronics required for this invention are well-known to one of ordinary skill in the art and are commercially available. Auxiliary electronic devices suitable for use in this invention include the following components:

| Component | Source | Catalog Number |
|---|---|---|
| Mosfet Drivers | International Rectifier El Segundo, CA | IRLD024 |
| Op-Amp | National Semiconductor Santa Clara, CA | LM358 |
| Status LED | Hewlett-Packard Newark Electronics Schaumburg, IL | HLMPD150 |
| Pressure Sensor | Sensym, Inc. Milpitas, CA | SDX15D4 |

Figure 3:
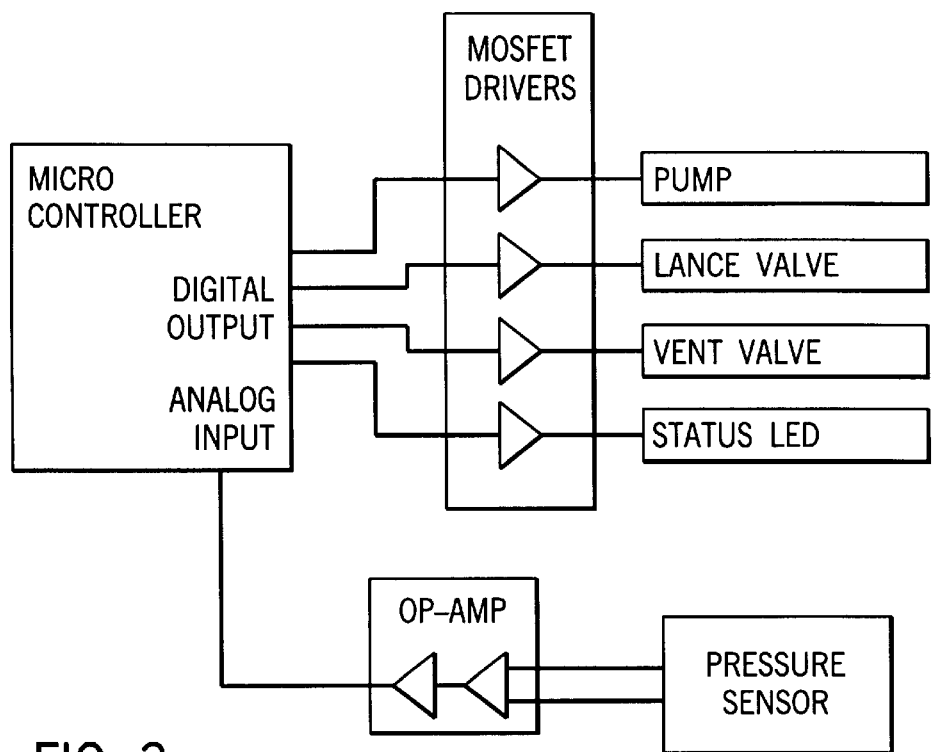
FIG. 3 is a block diagram illustrating the electronics of the preferred embodiment.

FIG. 3 illustrates by way of a block diagram how the foregoing electronic components can be arranged to carry out the method of the present invention.

Figure 2:
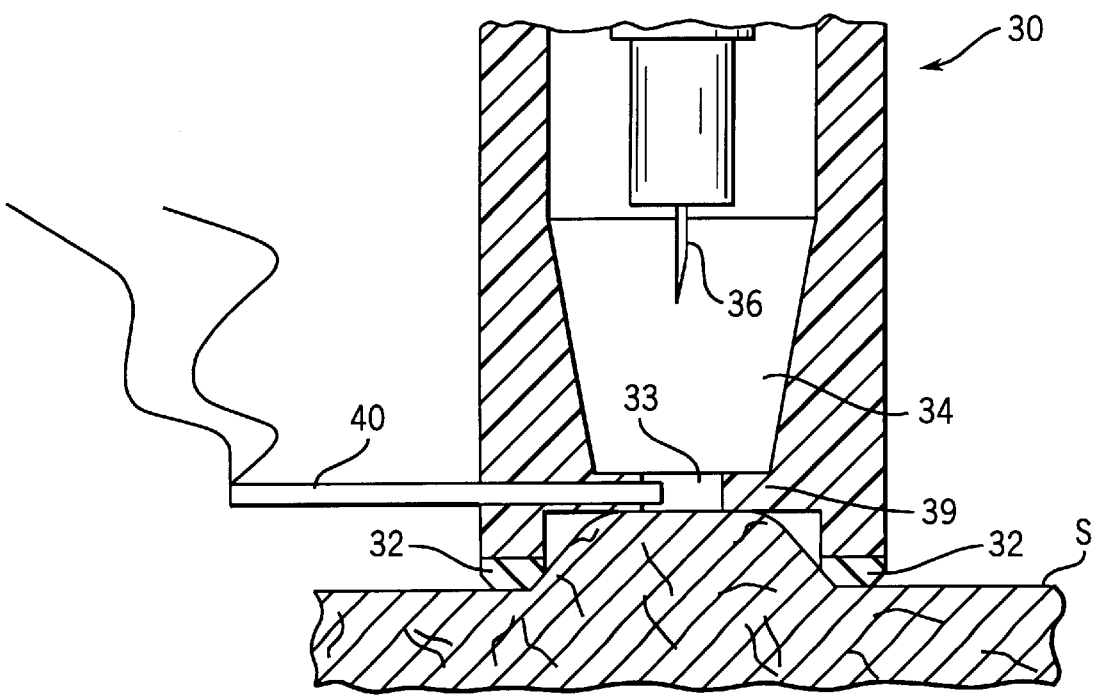
FIG. 2 is a schematic diagram illustrating how a vacuum causes a portion of the skin to become stretched prior to the formation of an opening in the skin from which the sample of blood is extracted.
Figure 4:
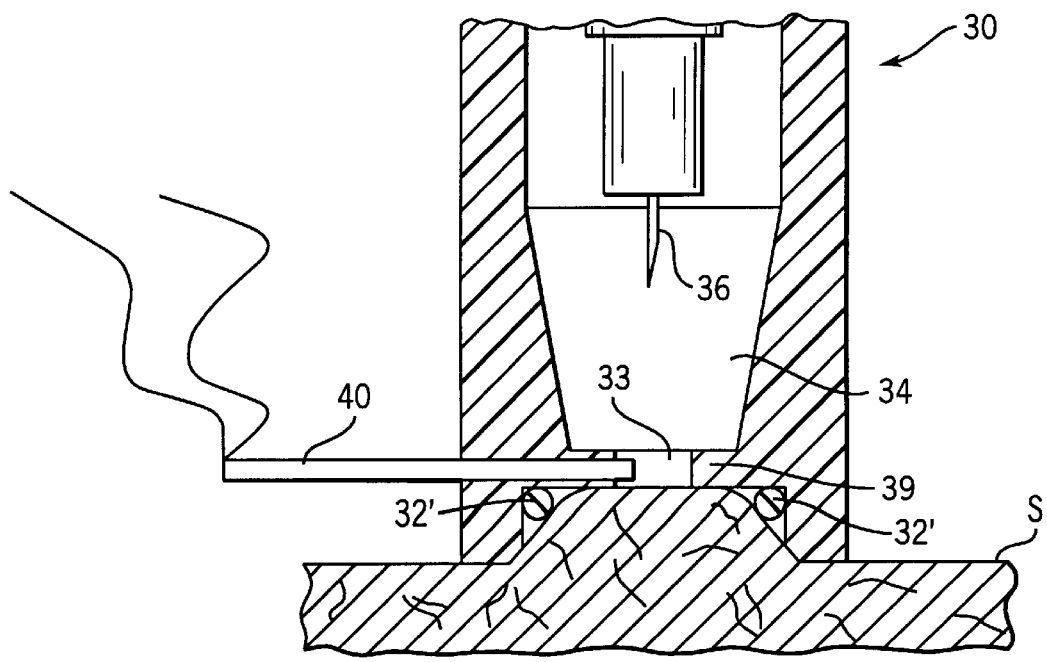
FIG. 4 is a schematic diagram illustrating an alternative seal for the vacuum of the device of the present invention.

Operation of the blood extraction device 10 will now be described. Referring now to FIGS. 1, 2 and 3, the nosepiece 30 of the lancing assembly 16 is applied to the surface of the skin, designated herein by the letter "S". The end of the nosepiece 30 that contacts the skin is equipped with a seal 32. The purpose of the seal 32 is to prevent air from leaking into blood extraction chamber 34, so that the vacuum pump 14 can provide sufficient suction action for increasing the availability of blood to the area of the skin from which the sample is to be extracted, stretching the skin, and extracting the sample of blood from the unobstructed opening in the skin. The seal 32 surrounds an opening 33 in the nosepiece 30. The opening 33 in the nosepiece allows communication between the surface of the skin and a blood extraction chamber 34 in the nosepiece 30. The seal 32 is preferably made of a rubber or an elastomeric material. FIG. 4 illustrates an alternative position for the seal 32. In FIG. 4, the seal is designated by the reference numeral 32'. The remaining parts of FIG. 4 are the same as those of FIG. 2, and , accordingly, retain the same reference numerals as were used in FIG. 2.

The switch 22 is actuated, typically by being pressed, thereby activating the electronics 20, which starts the vacuum pump 14. The vacuum pump 14 then provides a suction action. The suction action of the vacuum pump 14 causes the skin circumscribed by the seal 32 to become engorged with blood.

Engorgement of the skin with blood is accompanied by a stretching of and rising up of the skin up to opening 33.

After an appropriate period of time, which is typically pre-set by the programmer of the electronics, the lancing assembly 16 is triggered, thereby causing the lancet 36 to penetrate the skin that has risen up to the opening 33 and that is engorged with blood. The lancet 36 is preferably triggered automatically, by a solenoid valve 38 that causes a vacuum-actuated piston (not shown) to trigger the lancet 36. The lancet 36 is then retracted, preferably automatically. Thereupon, the blood flows out of the unobstructed opening resulting from the lancet 36, and, aided by the vacuum generated by the vacuum pump 14, is collected. When sufficient blood has been collected or a pre-set time interval has passed, the electronics 20 causes the vacuum pump 14 to stop. The device 10 can then be removed from the surface of the skin after another solenoid valve (not shown because it is hidden under solenoid valve 38) is opened to vent the vacuum to allow ease of removal of the device from the surface of the skin. Solenoid valves suitable for use with the apparatus described herein are commercially available from The Lee Company, Essex, Conn. and have the part number LHDA0511111H.

The blood is preferably directly collected on the application zone of a glucose detector, e.g., a reflectance strip or biosensor. The blood can then be used as the sample for a determination of glucose concentration in blood. Alternatively, the blood can be collected by other collection devices, such as, for example, a capillary tube or absorbent paper.

The apparatus of the present invention can include a glucose detector for analyzing the blood sample extracted by the apparatus. Glucose detectors are well-known in the art. With respect to glucose monitoring, there are two major categories of glucose detectors—reflectometers and biosensors. Representative examples of reflectometers suitable for this invention are described in U.S. Pat. No. 4,627,445, incorporated herein by reference. Representative examples of biosensors suitable for this invention are described in U.S. Pat. No. 5,509,410, incorporated herein by reference.

The glucose detector is preferably disposed in the nosepiece 30 of the lancing assembly 16. The glucose detector must be located at a position sufficiently close to the site of blood extraction so that the quantity of extracted blood collected will be sufficient to carry out a standard glucose monitoring test. Typically, this distance will preferably be no more than 5 mm from the site of blood extraction, more preferably no more than 3 mm from the site of blood extraction, most preferably no more than 1 mm from the site of blood extraction. Care must be taken in the placement of the glucose detector so that the detector does not adversely affect the vacuum, when a vacuum is employed to aid in the extraction of blood. In addition, the glucose detector 40 should be modified, if necessary, so that the blood collected in the collection zone of the glucose detector is capable of being used to activate the glucose detector.

FIG. 2 also illustrates a manner for disposing a glucose detector 40 in the nosepiece 30 of the lancing assembly 16.

One embodiment of the glucose detector 40 of this invention involves a multiple-layer element comprising:

(a) a layer capable of receiving blood and transporting the blood received by means of chemically aided wicking;

(b) a layer capable of detecting the presence of analyte or measuring the amount of analyte in blood; and (c) a layer that can be placed in contact with a meter, the meter-contactable layer overlying the blood-transporting layer, said layer (a) capable of transporting blood to said layer (b).

One preferred embodiment of the glucose detector 40 of this invention involves a multiple-layer element, which comprises:

(a) a covering layer having an opening therein;

(b) a layer, overlying the covering layer, capable of receiving blood through the opening in the covering layer and transporting blood by means of chemically aided wicking;

(c) a layer that can be placed in contact with a meter, the meter-contactable layer overlying the blood-transporting layer; and (d) a layer capable of detecting the presence of analyte or measuring the amount of analyte in blood, which layer is disposed between the covering layer and the meter-contactable layer and is capable of receiving blood from the blood-transporting layer.

Figure 11A:
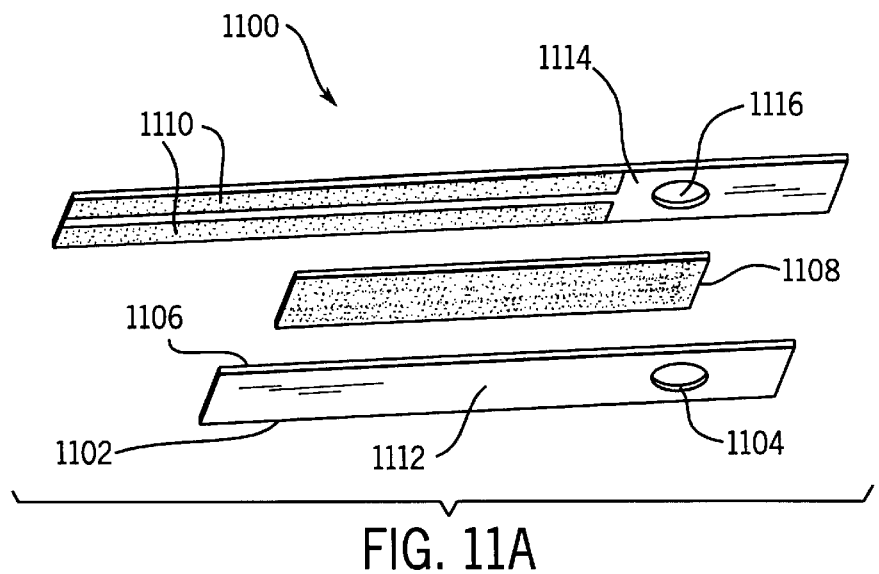
FIGS. 11A and 11B are exploded perspective views of a multiple-layer element for collecting blood and detecting an analyte.
Figure 11B:
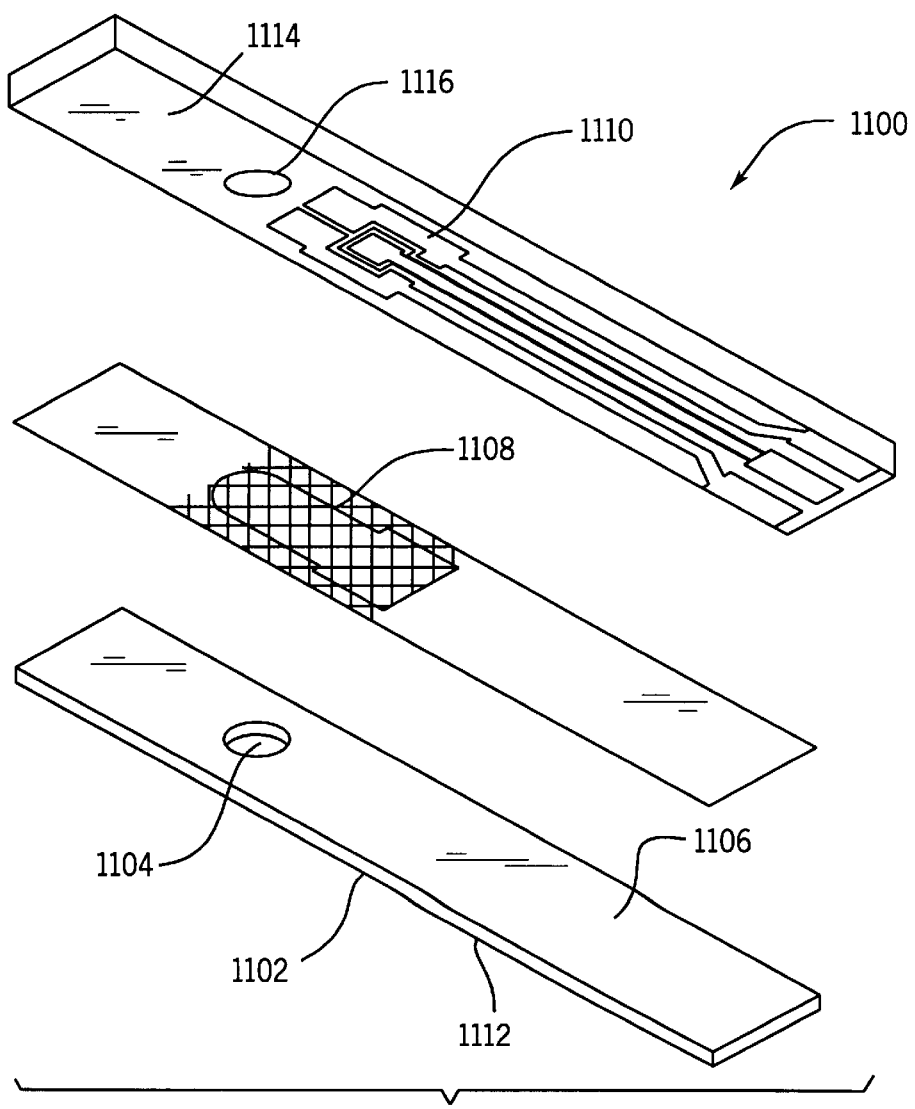

FIGS. 11A and 11B illustrate the aforementioned preferred embodiment of the multiple-layer element of this invention. During the course of discussing this embodiment, a discussion of the embodiment that does not require a covering layer will also be discussed. The multiple-layer element 1100 comprises a covering layer 1102 having an opening 1104 therein. To one major surface 1106 of covering layer 1102 is adhered a layer 1108 capable of transporting blood by means of chemically aided wicking to a detecting layer 1110. The other major surface 1112 of the covering layer 1102 is the surface that comes in close proximity to or may even contact the skin. Overlying layer 1110 is a meter-contactable layer 1114 having an opening 1116 therein.

The opening 1104 in the covering layer 1102 and the opening 1116 in the meter-contactable layer 1114 are aligned so that a lancet can pass through the opening 1104 and through the opening 1116 to pierce the skin. The blood-transporting layer 1108 can be designed to allow the lancet to pass through it or it can be positioned so that the lancet need not pass through it. The opening 1104 in the covering layer 1102 allows the blood-transporting layer 1108 to take up blood emerging from the opening in the skin formed by the lancet so that blood from that opening in the skin can be transported by means of a chemically aided wicking action to the detecting layer 1110.

The detecting layer 1110 can be disposed on a major surface of the covering layer 1102 or on a major surface of the meter-contactable layer 1114. The detecting layer 1110 comprises a layer or layers of chemicals, e.g., an enzyme, capable of reacting with an analyte in a biological fluid to produce either a measurable electrical response or a measurable optical response. U.S. Pat. Nos. 4,545,382; 4,711,245; and 5,682,884; all of which are incorporated herein by reference, describe detecting layers capable of generating a measurable electrical signal in response to glucose in blood. U.S. Pat. Nos. 4,935,346 and 4,929,545, both of which are incorporated herein by reference, describe detecting layers capable of producing a measurable change in reflectance in response to glucose in blood. An example of a detecting layer is described in U.S. Pat. No. 5,682,884. The detecting layer described in U.S. Pat. No. 5,682,884 comprises a first conductor and a second conductor extending along a support and further comprises a means for connection to readout circuitry. An active electrode, positioned to contact the liquid blood sample and the first conductor, comprises a deposit of an enzyme capable of catalyzing a reaction involving the analyte compound, e.g., glucose, in the liquid blood sample. Electrons are transferred between the enzyme-catalyzed reaction and the first conductor to create the current. A reference electrode is positioned to contact the liquid blood sample and the second conductor.

The covering layer 1102 is preferably formed from a hydrophobic material. The covering layer is preferably sufficiently flexible to conform to the remaining layers of the multiple-layer element. Representative examples of materials that are suitable for preparing the covering layer include, but are not limited to, polymeric materials, such as polyesters, polyimides, polyethylenes, polypropylenes, polycarbonates, polyacrylics, and combinations thereof.

The thickness of the covering layer 1102 is not critical, but preferably ranges from about 0.005 mm to about 2.0 mm. The surface dimensions of this layer are not critical, but the major surface dimension preferably ranges from about 5 mm to about 60 mm and the minor surface dimension preferably ranges from about 2 mm to about 30 mm. The layer is shown as being elongated and rectangular, but other shapes are also suitable, e.g., circular, elliptical, triangular, square, and other shapes.

The size of the opening 1104 in the covering layer 1102 must be sufficiently large to allow a lancet to pass therethrough into the skin of the patient. It is preferred that the opening 1104 be sufficiently large for a commercially available lancet to be used. Because commercially available lancet assemblies vary in how precisely the lancet is centered within the body of the lancet assembly, the opening 1104 in the covering layer 1102 is preferably sufficiently large to allow passage of the lancet, but not so large that it compromises the strength of the covering layer. Typically, the opening 1104 is no larger than one-half to three-quarters of the width of the covering layer 1102.

Although the embodiment in FIGS. 11A and 11B displays a covering layer, it is possible, but not preferred, to dispense with the covering layer entirely. In embodiments dispensing with the covering layer, the meter-contactable layer can have an opening therein through which the lancet can pass; alternatively, a sufficient amount of the meter-contactable layer can be trimmed such that a lancet will avoid striking the end of the meter-contactable layer prior to forming an opening in the skin. In this latter embodiment, the blood-transporting layer may or may not have an opening therein through which the lancet can pass.

The blood-transporting layer 1108 is preferably made from polymeric material, cellulosic material, natural fibrous material, or an equivalent material. Representative examples of polymeric materials suitable for the blood-transporting layer of this invention include, but are not limited to, polymers comprising amide monomeric units, e.g., nylon, ester monomeric units, alkylene monomeric units, e.g., polypropylene, polyethylene, cellulosic monomeric units, and combinations thereof. The blood-transporting layer can be a mesh. The mesh is preferably constructed of finely woven strands of polymeric material; however, any woven or non-woven material may be used, provided that the blood-transporting layer transports the blood to the detecting layer 1110 before the blood evaporates or clots. A fine mesh that is suitable for the multiple-layer element of this invention has a percent open area of from about 40 to about 45%, a mesh count of from about 95 to about 115 fibers per cm, a fiber diameter of from about 20 to about 40 $\mu$m, and a thickness of from about 40 to about 60 $\mu$m. A particularly preferred mesh is NY64 HC mesh, available from Sefar (formerly ZBF), CH-8803, Ruschlikon, Switzerland. A coarse mesh that is suitable for the multiple-layer element of this invention has a percent open area of from about 50 to about 55%, a mesh count of from about 45 to about 55 fibers per cm, a fiber diameter of from about 55 to about 65 $\mu$m, and a thickness of from about 100 to about 1000 $\mu$m. A preferred mesh is NY151 HC mesh, available from Sefar (formerly ZBF), CH-8803, Ruschlikon, Switzerland. Mesh characteristics are further described in U.S. Pat. No. 5,628,890, incorporated herein by reference.

The blood-transporting layer 1108 transports blood by means of a chemically aided wicking action. As used herein, the expression "chemically aided wicking action" refers to either:

(a) the flow of fluid along a material wherein the nature of the material itself is hydrophilic, such as, for example, cellulose;

(b) the flow of fluid along a material wherein at least one chemical substance is applied to the surface of the material, such as, for example, nylon coated with surfactant;

(c) the flow of fluid along a material that has been rendered hydrophilic by means of a chemical or physical process, such as, for example, treatment of polyester by means of corona discharge treatment, plasma treatment, flame treatment, or the like.

The purpose of the at least one chemical substance applied to the surface of the material of the blood-transporting layer is to promote the flow of fluid along the surface of the material. Chemical substances suitable for the foregoing purpose belong to the class of compounds commonly referred to as surfactants. Surfactants reduce the surface tension of the surface upon which they are coated and allow the coated surface to attract rather than repel fluids. A commercially available surfactant suitable for use in this invention is a fluorochemical surfactant having the trade designation "FC 170C FLUORAD", available from Minnesota Mining and Manufacturing Company, St. Paul, Minn. This surfactant is a solution of a fluoroaliphatic oxyethylene adduct, lower polyethylene glycols, 1,4-dioxane, and water. It has been found that approximately 1 to 10 µg surfactant per mg of blood-transporting layer is preferred. The preferred surfactant loading may vary depending upon the nature of the material of the blood-transporting layer and the surfactant used. The preferred amount can be determined empirically by observing flow of sample along the blood-transporting layer with different levels of surfactant loading. The surfactant may not be necessary if the mesh is made of hydrophilic material.

The blood-transporting layer 1108 is capable of allowing a sufficient amount of blood to uniformly flow through it at a rate sufficiently great that a sufficient amount of blood, e.g., 0.1 to 10 µl, preferably up to 2 µl, more preferably up to 1 µl, reaches the detecting layer 1110 before evaporation causes the size of the sample to be inadequate to provide a reading of analyte level within a reasonable time, e.g., up to five minutes. The blood-transporting layer 1108 can be adhered to the covering layer 1102 by means of hot melt adhesive on the major surface of the covering layer that faces the meter-contactable layer 1114. The blood-transporting layer 1108 can have a small opening formed in it, aligned with the path of the lancet and aligned with the openings in the covering layer 1102 and the meter-contactable layer 1114, whereby the possibility of the lancet striking a strand of mesh during the lancing operation is eliminated.

The covering layer 1102 and the blood-transporting layer 1108 are preferably arranged in such a way that blood emerging from the opening in the skin is not impeded from reaching the blood-transporting layer by the covering layer. Arrangements for the covering layer 1102 and blood-transporting layer 1108 suitable for use in this invention can be seen in FIGS. 11, 12, 13, 14, 15, 16A, 16B, and 17. It should be noted that FIG. 13 does not show a covering layer, but it should also be noted that FIG. 13 depicts the opposite side of the multiple-layer element of FIG. 12.

As shown in FIGS. 11A and 11B, the multiple-layer element has an opening 1104 formed in the covering layer 1102 and an opening 1116 formed in the meter-contactable layer 1114. The blood-transporting layer 1108 is disposed between the covering layer 1102 and the meter-contactable layer 1114.

In FIGS. 12, 13, 14, and 15, the blood-transporting layer 1108 is disposed directly over the opening 1104 in the covering layer 1102. In the detecting layer, electrical contacts are represented by the part having the reference numeral 1110a. In FIG. 13, the blood-transporting layer 1108 is disposed directly under the opening 1116 in the meter-contactable layer 1114. In FIGS. 12 and 13, the blood-transporting layer is a mesh having a relatively large number of openings per unit area. In FIG. 14, the blood-transporting layer is a mesh having a relatively small number of openings per unit area. In the embodiments shown in FIGS. 12, 13, and 14, there is the possibility that the lancet will hit one of the strands of mesh during the skin-opening step of the process. If a lancet hits one of the strands, the moving mass must have sufficient momentum to pierce the strand and the skin below it. The momentum of the moving mass is a function of the mass and the velocity of the moving components of the lancing assembly. The strength of the blood-transporting layer with respect to piercing will also determine the effectiveness of the lancing. The thickness and the material properties of the blood-transporting layer will determine its strength. It is preferred that the thickness and material properties of the mesh be such that a commercially available lancet can pierce the mesh.

In FIG. 15, the blood-transporting layer 1108 is disposed between the covering layer 1102 and the meter-contactable layer 1114 and is disposed directly under the opening 1104 in the covering layer 1102; however, the blood-transporting layer 1108 also has an opening 1118 formed therein. In the embodiment shown in FIG. 15, there is no possibility that the lancet will hit one of the strands of mesh during the skin-opening step of the process.

As shown in FIG. 16A, the meter-contactable layer 1114 has two openings 1116 and 1122 formed therein. The blood-transporting layer 1108 is offset from opening 1116 and directly over opening 1122. In this embodiment, the lancet passes through opening 1116 to form the opening in the skin. Then, some type of mechanical device, e.g., a spring, a solenoid, a pivot, or a four-bar linkage, causes the multiple-layer element to move a sufficient distance such that at least a portion of the blood-transporting layer 1108 is substantially directly over the opening formed in the skin, thereby minimizing the distance the blood needs to travel to reach the blood-transporting layer 1108 and at the same time eliminating the possibility of the lancet striking a strand of mesh during the lancing operation. The opening 1122 in the meter-contactable layer directly aligned with the blood-transporting layer 1108 can be used for application of vacuum to enhance the collection of blood. However, it should be noted that such an opening is optional, and can be dispensed with in other embodiments. See, for example, FIG. 16B, in which only one opening is formed in the meter-contactable layer. The movement of a multiple-layer element is described in copending application entitled METHOD AND APPARATUS FOR OBTAINING BLOOD FOR DIAGNOSTIC TESTS, Attorney's Docket No. 6005.US.P4, filed on evendate herewith, the entirety of which is incorporated herein by reference.

Figure 17:
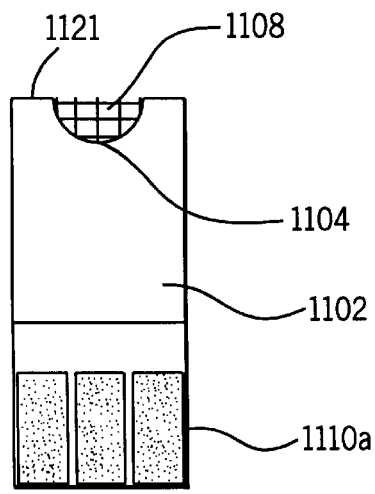
FIG. 17 is a top plan view of one embodiment of a multiple-layer element wherein the blood-transporting layer abuts one end of the element.

In FIG. 17, the blood-transporting layer 1108 abuts one end 1121 of the multiple-layer element. In the embodiment of FIG. 17, a lancet that passes through semi-circular opening 1104 can strike a strand of mesh during the lancing operation. The blood emerging from the opening formed in the skin has a minimal distance to travel to reach the blood-transporting layer 1108. Alternatively, after a lancet has formed an opening in the skin, the multiple-layer element can be moved in the manner described previously to facilitate taking up of blood by the blood-transporting layer 1108.

The detecting layer 1110 preferably comprises an electrochemical detector, e.g., a biosensor, or an optical detector, e.g., a reflectance detector. The detecting layer 1110 is supported on either the covering layer 1102 or on the meter-contactable layer 1114.

Detecting layers of the electrochemical type are preferably non-porous. Detecting layers of the optical type are preferably porous. It is preferred that the detecting layer be flexible, so that it will conform to whichever layer to which it is applied, the covering layer 1102 or the meter-contactable layer 1114. Detecting layers of the electrochemical type can be transparent or non-transparent. Detecting layers of the optical type are preferably reflective.

The detecting layer 1110 contains the reagents required for the chemical reaction required to provide an indication of the concentration or presence of analyte. In the case of glucose monitoring, these reagents include, but are not limited to, ferrocene, ferricyanide, glucose oxidase, glucose dehydrogenase, and peroxidases. Detecting layers of the electrochemical type preferably comprise a member selected from the group consisting of carbon, platinum, gold, palladium, silver chloride, and silver. Detecting layers of the reflectance type preferably comprise a member selected from the group consisting of dyes and enzymes.

As stated previously, a typical detecting layer comprises a first conductor and a second conductor extending along a support and further comprises a means for connection to readout circuitry. An active electrode, positioned to contact the liquid blood sample and the first conductor, comprises a deposit of an enzyme capable of catalyzing a reaction involving the analyte compound, e.g., glucose, in the liquid blood sample. Electrons are transferred between the enzyme-catalyzed reaction and the first conductor to create the current. A reference electrode is positioned to contact the liquid blood sample and the second conductor.

In a preferred embodiment of a detecting layer for the multiple-layer element of this invention, an electron mediator, e.g., a ferrocene, is included in the active electrode deposit to effect the electron transfer. The compound being detected is glucose and the enzyme is glucose oxidase or glucose dehydrogenase. The active electrode and the reference electrode are coatings applied to the covering layer 1102 or to the meter-contactable layer 1114. For example, the active electrode is formed by printing (e.g., screen printing) an ink comprising a conductive compound, the enzyme, and the mediator, and the reference electrode is also formed by printing (e.g., screen printing). The means for connecting to the readout circuit are positioned toward one end of the covering layer 1102 or the meter-contactable layer 1114, and the electrodes are positioned remote from that end. Additional variations of the foregoing embodiment are described in the previously incorporated U.S. Pat. No. 5,682,884.

The meter-contactable layer 1114 is preferably made from a polymeric material. Representative examples of polymeric material suitable for preparing the meter-contactable layer include polymers comprising acrylic monomeric units, methacrylic monomeric units, acrylate monomeric units, methacrylate monomeric units, vinyl chloride monomeric units, and combinations of the foregoing. Other polymers suitable for preparing the meter-contactable layer include polyesters. The functions of the meter-contactable layer are to (1) provide a surface on which to print the detecting layer 1110, (2) provide alignment of the opening or openings in the multiple-layer element with the lancet, (3) provide contact of the multiple-layer element with the meter for the purpose of reading the signal from the detecting portion of the multiple-layer element, (4) provide a rigid layer so that the multiple-layer element can be easily picked up and placed in contact with the meter, and, in the case of a detector measuring an optical response, provide a surface to contact against a meter, which contains a light source and means for reading the glucose signal from the detecting layer.

The size of the opening 1116 in the meter-contactable layer 1114 must be sufficiently large to allow a lancet to pass therethrough into the skin of the patient. It is preferred that the opening 1116 be sufficiently large for a commercially available lancet to be used. Because commercially available lancet assemblies vary in how precisely the lancet is centered within the body of the lancet assembly, the opening 1116 in the meter-contactable layer 1114 is preferably sufficiently large for passage of the lancet, but not so large that it compromises the strength of the meter-contactable layer. Typically, the opening 1116 is no larger than one-half to three-quarters of the width of the meter-contactable layer 1114.

Although the meter-contactable layer 1114 shown in FIGS. 11A and 11B displays an opening 1116, it is possible, but not preferred, to dispense with the opening 1116, so long as a sufficient amount of the meter-contactable layer 1114 is trimmed such that a lancet will avoid striking the end of the meter-contactable layer prior to passing through the opening 1104 in the covering layer 1102. In this embodiment, the blood-transporting layer 1108 may or may not have an opening therein.

The following table lists suitable ranges for the dimensions of the layers of the multiple-layer element of this invention. It is not intended that the dimensions of the layers of the multiple-layer element of this invention be limited to the ranges listed in the following table.

| Layer | Major surface dimension (mm) | Minor surface dimension (mm) | Thickness (mm) |
| --- | --- | --- | --- |
| Covering | 5 to 60 | 2 to 30 | 0.005 to 2.0 |
| Blood-transporting | 5 to 60 | 2 to 30 | 0.005 to 0.5 |
| Detecting | 5 to 60 | 2 to 30 | 0.001 to 0.5 |
| Meter-contactable | 5 to 60 | 2 to 30 | 0.05 to 2.0 |

The multiple-layer element is preferably sufficiently rigid so that it can be easily handled by the user. In the preferred embodiments, either the covering layer 1102 or the meter-contactable layer 1114 or both of these layers are made of a material that is sufficiently rigid to support the blood-transporting layer 1108 and the detecting layer 1110. The last two mentioned layers can be extremely flexible and of minimal rigidity.

The porosity of the layers of the multiple-layer element is dependent upon the positioning and functionality of the layer. The covering layer 1102 and the meter-contactable layer 1114 are preferably sufficiently non-porous to form a well or chamber for the blood. The blood-transporting layer 1108 is preferably sufficiently porous to allow blood to flow uniformly and rapidly therethrough to the detecting layer 1110. The porosity of the detecting layer is not critical; it can be porous or non-porous depending upon the design selected by the manufacturer.

The surface dimensions, e.g., length, of the blood-transporting layer 1108 are preferably less than those of the layer on which the detecting layer 1110 is printed, so that in the case of electrochemical sensors, the electrical contacts 1110a on the detecting layer 1110 are exposed to facilitate insertion into the meter.

The surface dimensions, e.g., length, of the meter-contactable layer 1114 are preferably larger than those of the covering layer 1102 so that electrical contacts, in the case of electrochemical sensors printed on the meter-contactable layer, are exposed for insertion into the meter. The opacity of the meter-contactable layer is not critical unless photometric detection is used.

Figure 18:
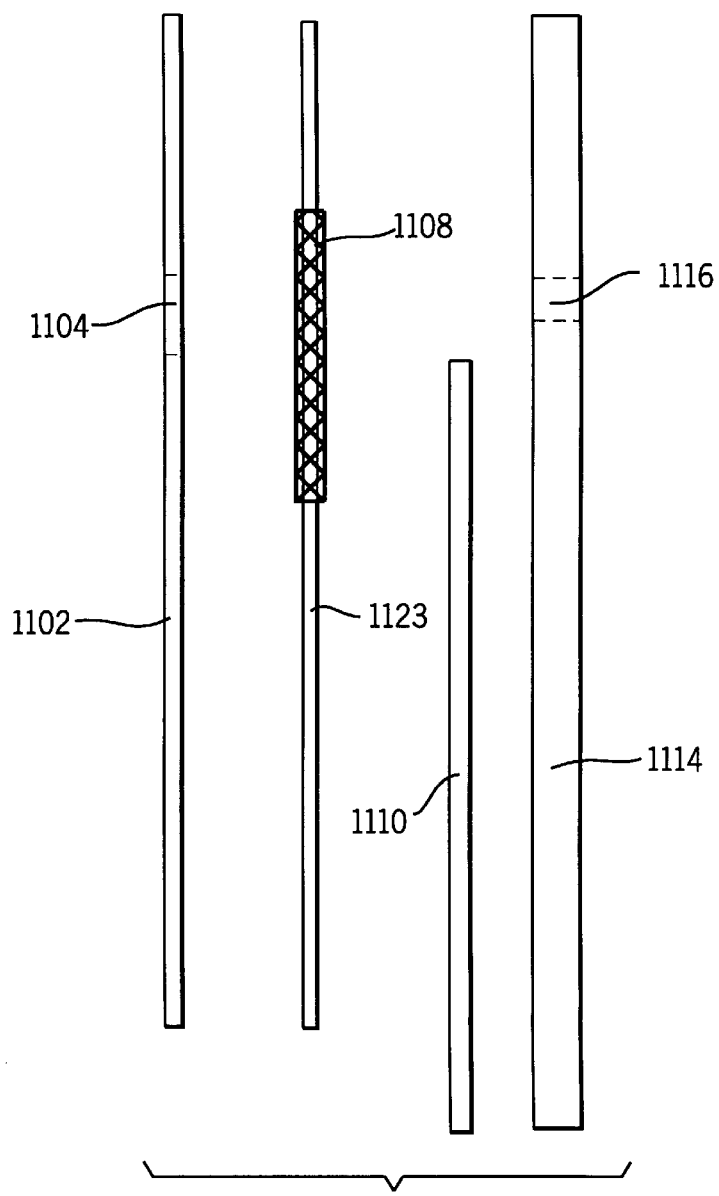
FIG. 18 is an exploded elevational view of a multiple-layer element of this invention.

As stated previously, an optional overcoat layer 1123 (see FIG. 18) can be interposed between the covering layer 1102 and the meter-contactable layer 1114 to restrict the flow of blood in the blood-transporting layer 1108. The overcoat layer can be prepared by means of a material that is initially in a liquid form or in a form capable of penetrating the interstices of a mesh. This material is preferably a hydrophobic electrically insulating ink. This material is preferably applied by screen printing over a portion of the periphery of the blood-transporting layer (which is preferably in the form of a mesh), thereby surrounding and defining a suitable path for the sample of blood to travel from the point it contacts the blood-transporting layer to the detecting layer 1110. See U.S. Pat. No. 5,628,890 for additional discussion concerning how the overcoat layer holds down and fixes the mesh layer in place. The overcoat layer 1123 and the blood-transporting layer 1108 are substantially coplanar. As used herein, the term "coplanar" means that at least one surface of each of two materials resides in the same plane. Substantial coplanar positioning of these layers is preferred because the blood-transporting layer 1108 spreads blood in all directions. In order to limit the spread of blood in undesired areas of the multiple-layer element, the overcoat layer 1123 acts as a barrier to flowing blood. The blood-transporting layer 1108 is adhered to the meter-contactable layer 1114 by means of embedding the edges of the blood-transporting layer 1108 with the overcoat layer 1123. FIG. 18 illustrates the relationship between the planes of the optional overcoat layer 1123 and the blood-transporting layer 1108. As used herein, the expression "substantially coplanar" includes both the situation wherein at least one major surface of the overcoat layer 1123 and at least one major surface of the blood-transporting layer 1108 are in the same plane and the situation wherein at least one major surface of the overcoat layer 1123 extends slightly beyond at least one major surface of the blood-transporting layer 1108. True coplanarity, i.e., the former situation, is difficult to achieve primarily because of manufacturing conditions. Substantial coplanarity, i.e., the latter situation, is more likely to be achieved under actual manufacturing conditions. FIG. 18 illustrates the more likely manufacturing result. However, it is preferred that the overcoat layer 1123 and the blood-transporting layer 1108 approach true coplanarity as much as possible so that the volume of blood needed to be extracted is as small as possible.

Method for Preparing the Multiple-Layer Element

The multiple-layer element is preferably mass-produced. However, the following method can be used for the manufacture of a single multiple-layer element.

The meter-contactable layer 1114 can be provided in the form of a sheet. In a typical construction, the meter-contactable layer 1114 can be a sheet of polyvinyl chloride. The detecting layer 1110 can be screen printed onto the meter-contactable layer 1114. The detecting layer 1110 can be a biosensor of a type described in U.S. Pat. No. 4,545,382, incorporated herein by reference. In a preferred embodiment, the electrodes of the detecting layer 1110 contain a biologically active substance that reacts with glucose, preferably glucose oxidase or glucose dehydrogenase, and an electrically conductive material, preferably carbon, which carries the electrical signal produced by the reaction of glucose with the biologically active substance to an electrical connector in the meter. The generation of the electrical signal may be aided by compounds known as mediators, which increase the electrical signal. See Ferrocene-Mediated Enzyme Electrode for Amperometric Determination of Glucose, Anal. Chem. 1984, 56, 667–671. The electrical circuit is completed with at least one other electrically conductive material, preferably silver chloride, that is referred to as a reference or counter electrode.

The blood-transporting layer 1108 is then placed in a position such that it will be in fluid communication with the detecting layer 1110. The covering layer 1102 can then be adhered to the blood-transporting layer by means of a hot-melt adhesive.

Operation

Figure 19A:
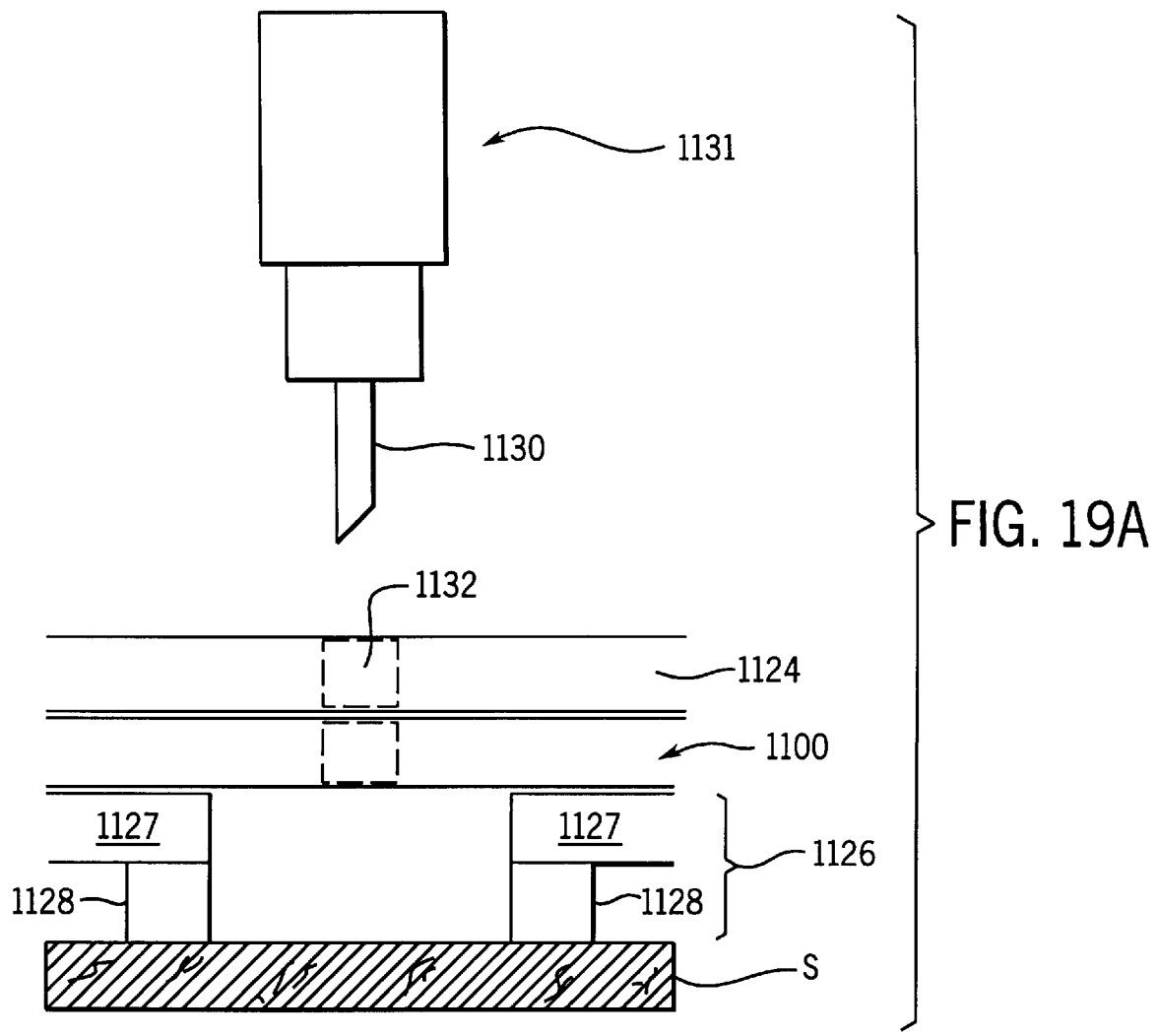
FIGS. 19A, 19B, 19C, and 19D schematically illustrate a procedure by which the method of this invention is carried out with the multiple-layer element of this invention.
Figure 19B:
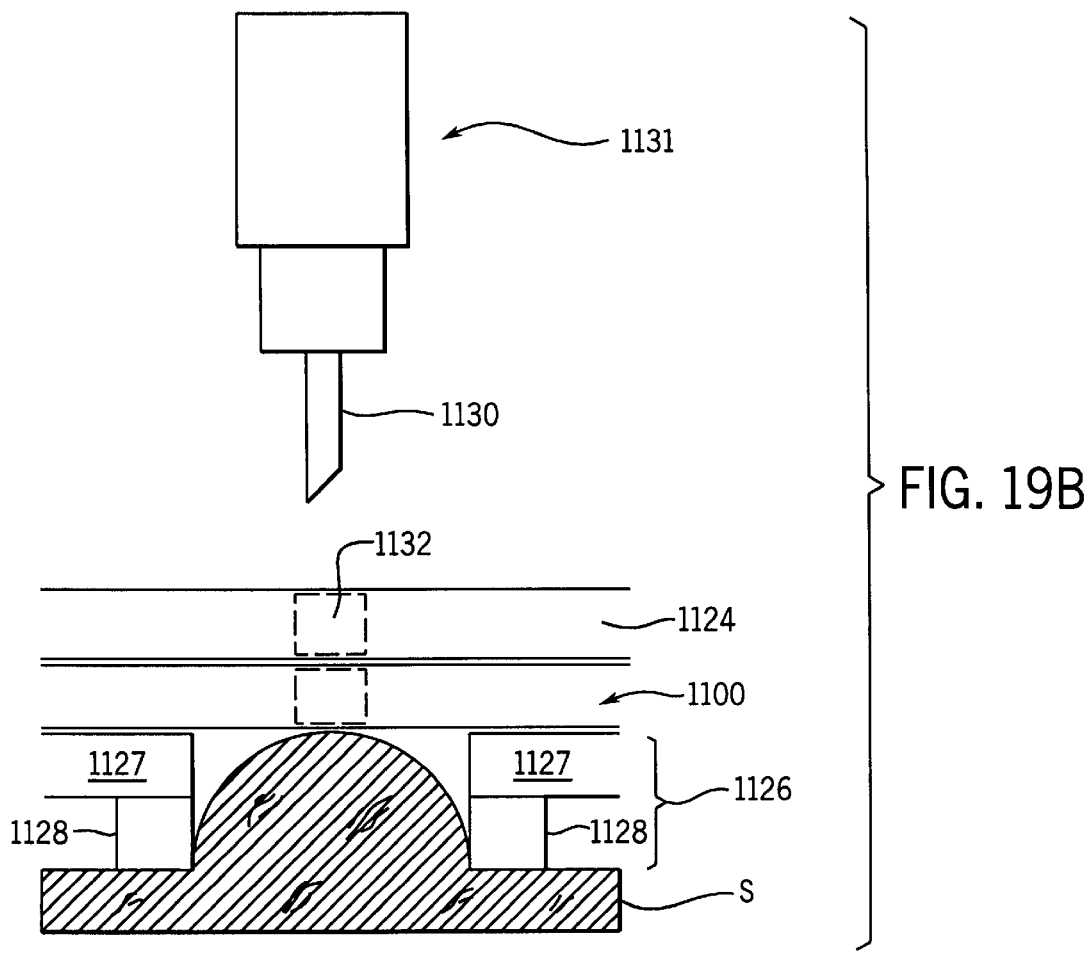
Figure 19C:
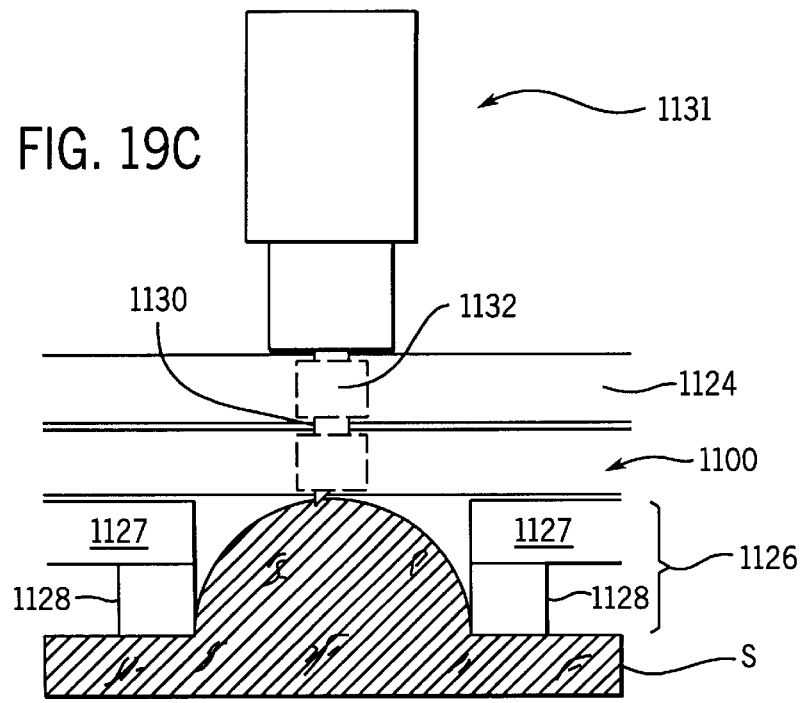
Figure 19D:
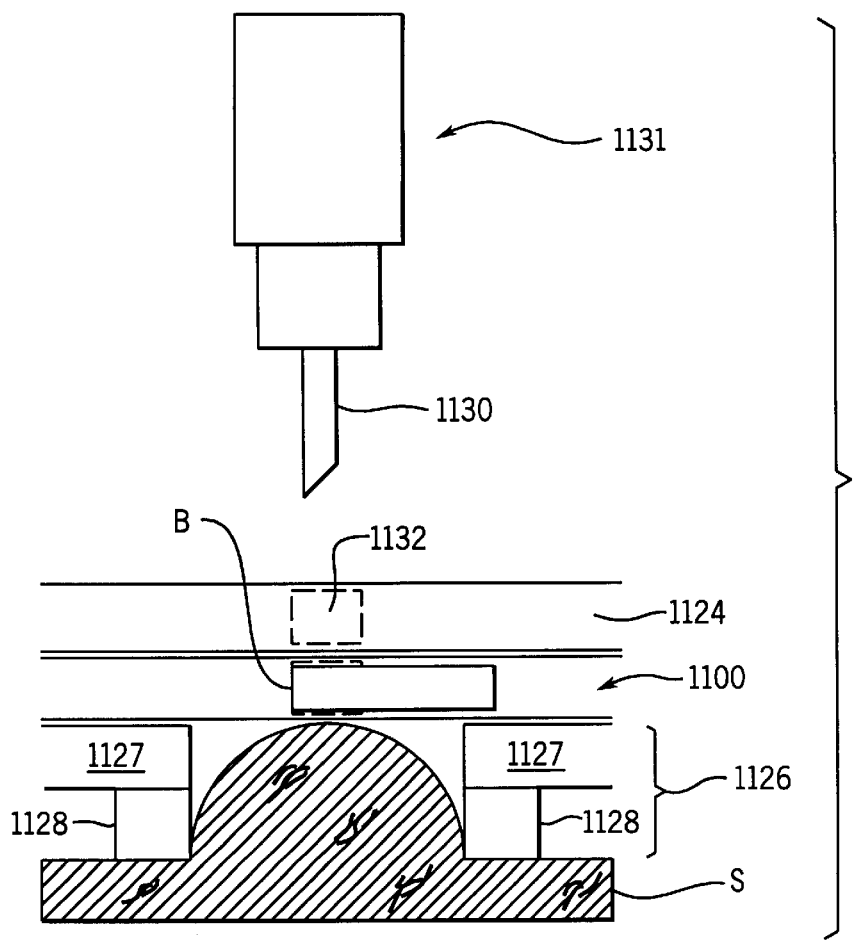

Referring now to FIGS. 11A and 11B, which illustrate the components of the multiple-layer element in detail, and FIGS. 19A, 19B, 19C, and 19D, which illustrate how the multiple-layer element operates, in order to use the article of this invention for detecting the presence or amount of analyte in a sample of blood, the multiple-layer element 1100 is placed between a lancet stop 1124 and the nosepiece assembly 1126 of the blood collecting apparatus. The nosepiece assembly 1126 comprises a nosepiece 1127 and a seal 1128. The opening 1104 in the covering layer 1102 and the opening 1116 in the meter-contactable layer 1114 are aligned with a lancet 1130 of a lancing assembly 1131. The seal 1128 of the nosepiece assembly 1126 of the blood collecting apparatus is placed against the skin, "S". FIG. 19A illustrates the apparatus prior to application of vacuum. FIG. 19B illustrates the apparatus after application of vacuum, after the skin is stretched and drawn into contact with the covering layer 1102 of the multiple-layer element. The vacuum is applied for a sufficient period of time to cause blood to pool in the skin, which is drawn up into the nosepiece 1127. The lancing assembly is then actuated and the lancet 1130 passes through an opening 1132 in the lancet stop 1124 and the openings in the multiple-layer element (shown in phantom in FIGS. 19A, 19B, 19C, and 19D and designated by reference numerals 1104 and 1116 in FIGS. 11A and 11B). Then the lancet penetrates the skin, forming an opening therein. See FIG. 19C. Then the lancet is retracted, thereby forming an unobstructed opening in the skin. The blood, "B", emerges from the unobstructed opening in the skin assisted by vacuum, and contacts the blood-transporting layer 1108, flows along the blood-transporting layer, whereupon it reaches the detecting layer 1110. See FIG. 19D. A chemical reaction occurs at the surface of the detecting layer. The output of the chemical reaction can be read at the electrical contacts 1110a of the detecting layer 1110. After the multiple-layer element is filled, the vacuum is released and the skin comes away from the nosepiece.

In the case of an electrochemical sensor, the meter-contactable layer 1114 must physically contact the meter (not shown) in order to have the sensor, i.e., the detecting layer 1110, make electrical contact with the meter, such as by insertion into an electrical connector. The meter-contactable layer can also serve to physically align the multiple-layer element with the meter in order to properly align the lancet with the opening 1116 in the meter-contactable layer. In the case of the reflectance strip, the meter-contactable layer must be mounted in the meter to allow alignment of the light source and the detector of the meter with the reflectance strip, as well as allowing physical alignment of the multiple-layer element with the meter so that the lancet is properly aligned with the opening 1116 in the meter-contactable layer.

While not preferred, it is also possible to provide a workable multiple-layer element that dispenses with the blood-transporting layer. In order to eliminate the blood-transporting layer, the meter-contactable layer and the covering layer can be disposed in such a manner that blood can flow between them to the detecting layer by means of capillary action. In one embodiment involving flow by means of capillary action, the major surface of the meter-contactable layer facing the major surface of the covering layer and the major surface of the covering layer facing the major surface of the meter-contactable layer should be hydrophilic in nature. At least one of the foregoing major surfaces, and preferably both of the foregoing major surfaces, can either be made of a hydrophilic material or can be coated with a hydrophilic material, such as, for example, a surfactant. The hydrophilicity of these layers will cause the blood extracted to flow in the space between the meter-contactable layer and the covering layer to the detecting layer. Thus, it is clear that the blood-transporting layer can be eliminated. In this embodiment, the meter-contactable layer must be of sufficient length so that a capillary channel can be formed between the meter-contactable layer and the covering layer. Thus, if the covering layer is of such a length as to require an opening through which the lancet can pass, it is preferred that the meter-contactable layer also be of such a length as to require an opening through which the lancet can pass. The capillary channel can be, in effect, formed by means of the overcoat layer, which causes a space of capillary width to be formed between the meter-contactable layer and the covering layer.

By using the multiple-layer element of this invention, the collection of blood can be carried out in a highly efficient manner. Improving the efficiency of collection will reduce the period of time required to obtain blood for analytical purposes.

FIGS. 5, 6, 7, 8, 9, and 10 illustrate various alternative embodiments of the apparatus of this invention. In FIG. 5, blood extraction device 100 comprises a housing 102. The housing 102 is separable into two portions, a receiving portion 102a and a projecting portion 102b. A gasket 104 is provided to seal the portions 102a and 102b of the housing 102 and to aid in separation of the receiving portion 102a from the projecting portion 102b. The receiving portion 102a forms a tight fit with the projecting portion 102b by means of friction. Projecting elements 102c and 102d are used to guide the projecting portion 102b into the receiving portion 102a. Disposed within the housing 102 are a vacuum pump (not shown), a lancing assembly 108, a battery (not shown), and electronics (not shown). A switch 109 is provided to activate the electronics.

The vacuum pump is connected to the lancing assembly 108 by an evacuation tube (not shown). A check valve (not shown) is placed between the vacuum pump and the lancing assembly 108.

During the process of obtaining the sample, the receiving portion 102a and the projecting portion 102b are fitted tightly together. The area of the receiving portion 102a of the housing 102 of the device 100 that is to contact the skin is equipped with a seal 110. The seal 110 surrounds an opening 112 in the receiving portion 102a. The opening 112 in the receiving portion 102a allows communication between the surface of the skin and a blood extraction chamber adjacent to a glucose detector 114, shown here in the shape of a strip. When in use, the device 100 is positioned so that the lancing assembly 108 is placed over the region on the surface of the skin from which the sample is to be obtained. In order to obtain the sample of blood, the receiving portion 102a of the housing 102 of the device 100 is placed against the skin, whereby the seal 110 allows a satisfactory vacuum to be effected. The switch 109 is actuated, typically by being pressed, thereby activating the electronics, which starts the vacuum pump. The vacuum pump then provides a suction action. The suction action of the vacuum pump causes the skin circumscribed by the seal 110 to become engorged with blood. Engorgement of the skin with blood is accompanied by a stretching of and rising up of the skin up to the opening 112. After an appropriate period of time, which is typically pre-set by the programmer of the electronics, the lancing assembly 108 is triggered, thereby causing the lancet 116 to penetrate the skin that has risen up to the opening 112 and that is engorged with blood. The lancet 116 is preferably triggered automatically, by a solenoid valve (not shown) that causes a vacuum-actuated piston (not shown) to trigger the lancet 116. The remaining steps of the process relating to collection of a sample of blood are substantially similar to the steps described in the embodiment shown in FIGS. 1, 2, 3, and 4.

In the embodiment shown in FIG. 5, the glucose detector 114 is inserted into a slot 118 in the projecting portion 102b of the housing 102. The receiving portion 102a of the housing 102 causes the glucose detector 114 to be moved into its proper position for testing. The results obtained from the glucose detector 114 can be displayed on a screen 120, typically a conventional liquid crystal digital display. The receiving portion 102a is separated from the projecting portion 102b when the lancet 116 or glucose detector 114 is being replaced. The receiving portion 102a is fitted tightly to the projecting portion 102b during the process of obtaining a sample of blood.

The relative positions of the vacuum pump, the battery, the electronics, the evacuation tube, the check valve, the solenoid valves, and the vacuum-actuated piston are substantially similar to the relative positions of these components as described in the embodiments shown in FIGS. 1 and 2.

In FIG. 6, blood extraction device 200 comprises a housing 202. The housing 202 comprises a door portion 202a that is attached to the remaining portion 202b of the housing 202 by a hinge 206. A gasket 207 is provided to seal the housing 202 when the door portion 202a is closed. The door portion 202a can be closed by pivoting it around the hinge 206. When the door portion 202a is closed, the convex portion 202c of the door portion 202a fits precisely into the concave portion 202d of the remaining portion 202b of the housing 202. The remaining edges of the door portion 202a fit tightly against the remaining edges of the remaining portion 202b of the housing 202. Disposed within the housing 202 are a vacuum pump (not shown), a lancing assembly 208, a battery (not shown), and electronics (not shown). A switch (not shown) is provided to activate the electronics. The vacuum pump is connected to the lancing assembly 208 by an evacuation tube (not shown). A check valve (not shown) is placed between the vacuum pump and the lancing assembly 208.

During the process of obtaining the sample, the door portion 202a is closed. The area of the door portion 202a of the housing 202 of the device 200 that is to contact the skin is equipped with a seal (not shown). The seal surrounds an opening 212 in the door portion 202a. The opening 212 in the door portion 202a allows communication between the surface of the skin and a blood extraction chamber adjacent to a glucose detector 214, shown here in the shape of a strip. When in use, the device 200 is positioned so that the lancing assembly 208 is placed over the region on the surface of the skin from which the sample is to be obtained. In order to obtain the sample of blood, the door portion 202a of the housing 202 of the device 200 is placed against the skin, whereby the seal allows a satisfactory vacuum to be effected. The switch is actuated, typically by being pressed, thereby activating the electronics, which starts the vacuum pump. The vacuum pump then provides a suction action. The suction action of the vacuum pump causes the skin circumscribed by the seal to become engorged with blood.

Engorgement of the skin with blood is accompanied by a stretching of and rising up of the skin up to the opening 212. After an appropriate period of time, which is typically pre-set by the programmer of the electronics, the lancing assembly 208 is triggered, thereby causing the lancet 216 to penetrate the skin that has risen up to the opening 212 and that is engorged with blood. The lancet 216 is preferably triggered automatically, by a solenoid valve (not shown) that causes a vacuum-actuated piston (not shown) to trigger the lancet 216. The remaining steps of the process relating to collection of a sample of blood are substantially similar to the steps described in the embodiment shown in FIGS. 1, 2, 3, and 4.

In the embodiment shown in FIG. 6, the glucose detector 214 is inserted into slots 218a and 218b of the housing 202. The results obtained from the glucose detector 214 can be displayed on screen 220, typically a conventional liquid crystal digital display. The door portion 202a is opened when the lancet 216 or glucose detector 214 is being replaced. The door portion 202a is closed during the process of obtaining a sample of blood.

The relative positions of the vacuum pump, the battery, the electronics, the switch, the evacuation tube, the check valve, the seal, the solenoid valves, and the vacuum-actuated piston are substantially similar to the relative positions of these components as described in the embodiments shown in FIGS. 1 and 2.

Figure 7:
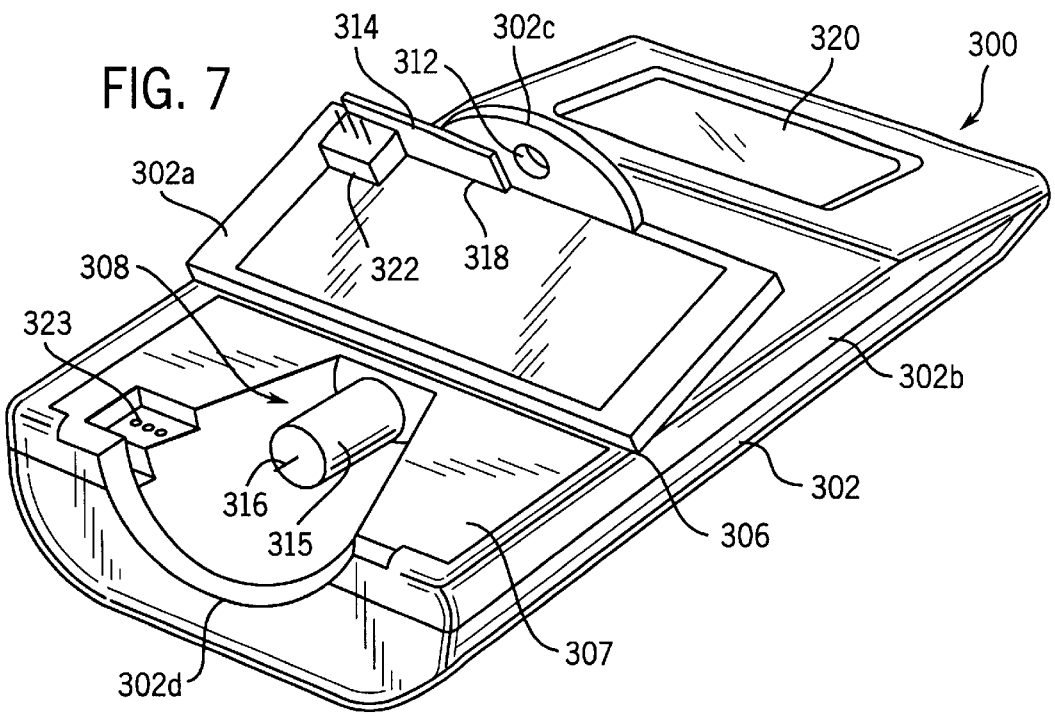
FIG. 7 is a perspective view of an embodiment of the apparatus of this invention. In this figure, the housing of the apparatus is open.

In FIG. 7, blood extraction device 300 comprises a housing 302. The housing 302 comprises a door portion 302a that is attached to the remaining portion 302b of the housing 302 by a hinge 306. A gasket 307 is provided to seal the housing 302 when the door portion 302a is closed. The door portion 302a can be closed by pivoting it around the hinge 306. When the door portion 302a is closed, the convex portion 302c of the door portion 302a fits precisely into the concave portion 302d of the remaining portion 302b of the housing 302. The remaining edges of the door portion 302a fit tightly against the remaining edges of the remaining portion 302b of the housing 302. Disposed within the housing 302 are a vacuum pump (not shown), a lancing assembly 308, a battery (not shown), and electronics (not shown). A switch (not shown) is provided to activate the electronics. The vacuum pump is connected to the lancing assembly 308 by an evacuation tube (not shown). A check valve (not shown) is placed between the vacuum pump and the lancing assembly 308. During the process of obtaining the sample, the door portion 302a is closed. The area of the door portion 302a of the housing 302 of the device 300 that is to contact the skin is equipped with a seal (not shown). The seal surrounds an opening 312 in the door portion 302a. The opening 312 in the door portion 302a allows communication between the surface of the skin and a blood extraction chamber adjacent to a glucose detector 314, shown here in the shape of a strip. When in use, the device 300 is positioned so that the lancing assembly 308 is placed over the region on the surface of the skin from which the sample is to be obtained. In order to obtain the sample of blood, the door portion 302a of the housing 302 of the device 300 is placed against the skin, whereby the seal allows a satisfactory vacuum to be effected. The switch is actuated, typically by being pressed, thereby activating the electronics, which starts the vacuum pump. The vacuum pump then provides a suction action. The suction action of the vacuum pump causes the skin circumscribed by the seal to become engorged with blood. Engorgement of the skin with blood is accompanied by a stretching of and rising up of the skin up to the opening 312. After an appropriate period of time, which is typically pre-set by the programmer of the electronics, the lancing assembly 308 is triggered, thereby causing the lancet 316 to penetrate the skin that has risen up to the opening 312 and that is engorged with blood. The lancet 316 is preferably triggered automatically, by a solenoid valve (not shown) that causes a vacuum-actuated piston (not shown) to trigger the lancet 316. The remaining steps of the process relating to collection of a sample of blood are substantially similar to the steps described in the embodiment shown in FIGS. 1, 2, 3, and 4.

In the embodiment shown in FIG. 7, the glucose detector 314 is inserted into a slot 318 of the housing 302. The results obtained from the glucose detector 314 can be displayed on screen 320, typically a conventional liquid crystal digital display. In FIG. 7, connections 322 for the electronics are shown. The door portion 302a is opened when the lancet 316 or glucose detector 314 is being replaced. The door portion 302a is closed during the process of obtaining a sample of blood.

The relative positions of the vacuum pump, the battery, the electronics, the switch, the evacuation tube, the check valve, the seal, the solenoid valves, and the vacuum-actuated piston are substantially similar to the relative positions of these components as described in the embodiments shown in FIGS. 1 and 2.

Figure 8:
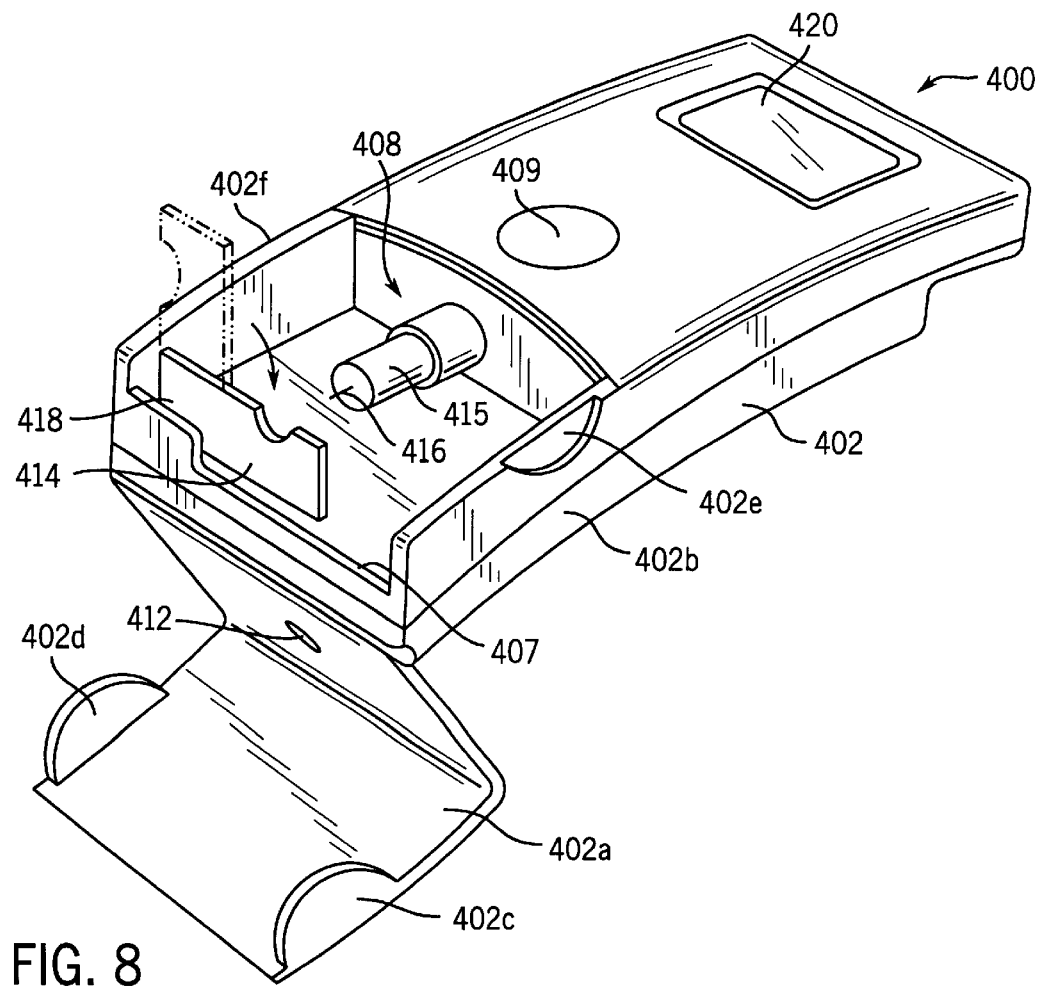
FIG. 8 is a perspective view of an embodiment of the apparatus of this invention. In this figure, the housing of the apparatus is open.

In FIG. 8, blood extraction device 400 comprises a housing 402. The housing 402 comprises a door portion 402a that is attached to the remaining portion 402b of the housing 402 by a hinge 406. A gasket 407 is provided to seal the housing 402 when the door portion 402a is closed. The door portion 402a can be closed by pivoting it around the hinge 406. When the door portion 402a is closed, the convex portions 402c and 402d of the door portion 402a fit precisely into the concave portions 402e and 402f, respectively, of the remaining portion 402b of the housing 402. The remaining edges of the door portion 402a fit tightly against the remaining edges of the remaining portion 402b of the housing 402. Disposed within the housing 402 are a vacuum pump (not shown), a lancing assembly 408, a battery (not shown), and electronics (not shown). A switch 409 is provided to activate the electronics. The vacuum pump is connected to the lancing assembly 408 by an evacuation tube (not shown). A check valve (not shown) is placed between the vacuum pump and the lancing assembly 408.

During the process of obtaining the sample, the door portion 402a is closed. The area of the door portion 402a of the housing 402 of the device 400 that is to contact the skin is equipped with a seal (not shown). The seal surrounds an opening 412 in the door portion 402a. The opening 412 in the door portion 402a allows communication between the surface of the skin and a blood extraction chamber adjacent to a glucose detector 414, shown here in the shape of a strip. When in use, the device 400 is positioned so that the lancing assembly 408 is placed over the region on the surface of the skin from which the sample is to be obtained. In order to obtain the sample of blood, the door portion 402a of the housing 402 of the device 400 is placed against the skin, whereby the seal allows a satisfactory vacuum to be effected. The switch 409 is actuated, typically by being pressed, thereby activating the electronics, which starts the vacuum pump. The vacuum pump then provides a suction action. The suction action of the vacuum pump causes the skin circumscribed by the seal to become engorged with blood. Engorgement of the skin with blood is accompanied by a stretching of and rising up of the skin up to the opening 412. After an appropriate period of time, which is typically pre-set by the programmer of the electronics, the lancing assembly 408 is triggered, thereby causing the lancet 416 to penetrate the skin that has risen up to the opening 412 and that is engorged with blood. The lancet 416 is preferably triggered automatically, by a solenoid valve (not shown) that causes a vacuum-actuated piston (not shown) to trigger the lancet 416. The remaining steps of the process relating to collection of a sample of blood are substantially similar to the steps described in the embodiment shown in FIGS. 1, 2, 3, and 4.

In the embodiment shown in FIG. 8, the glucose detector 414 is inserted into a slot 418 of the housing 402. In this embodiment, it is shown that glucose detector 14 can be rotated 90° between two positions to simplify insertion and replacement thereof. The results obtained from the glucose detector 414 can be displayed on screen 420, typically a conventional liquid crystal digital display. The door portion 402*a* is opened when the lancet 416 or glucose detector 414 is being replaced. The door portion 402*a* is closed during the process of obtaining a sample of blood.

The relative positions of the vacuum pump, the battery, the electronics, the evacuation tube, the check valve, the seal, the solenoid valves, and the vacuum-actuated piston are substantially similar to the relative positions of these components as described in the embodiments shown in FIGS. 1 and 2.

Figure 9:
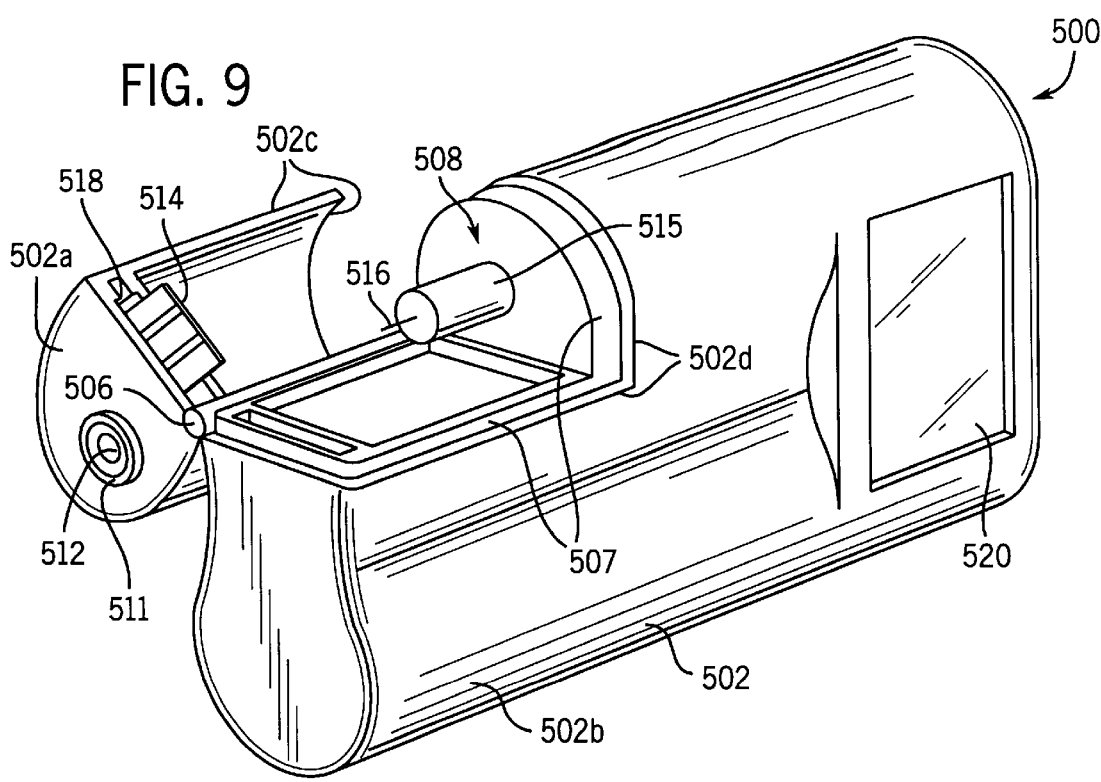
FIG. 9 is a perspective view of an embodiment of the apparatus of this invention. In this figure, the housing of the apparatus is open.

In FIG. 9, blood extraction device 500 comprises a housing 502. The housing 502 comprises a cover portion 502*a* that is attached to the remaining portion 502*b* of the housing 502 by a hinge 506. A gasket 507 is provided to seal the housing 502 when the cover portion 502*a* is closed. The cover portion 502*a* can be closed by pivoting it around the hinge 506. When the cover portion 502*a* is closed, edges 502*c* of the cover portion 502*a* tightly fit against edges 502*d* of the remaining portion 502*b* of the housing 502. Disposed within the housing 502 are a vacuum pump (not shown), a lancing assembly 508, a battery (not shown), and electronics (not shown). A switch (not shown) is provided to activate the electronics. The vacuum pump is connected to the lancing assembly 508 by an evacuation tube (not shown). A check valve (not shown) is placed between the vacuum pump and the lancing assembly 508.

During the process of obtaining the sample, the cover portion 502*a* is closed. The cover portion 502*a* of the housing 502 of the device 500 that is to contact the skin is equipped with a seal 511. The seal 511 surrounds an opening 512 in the cover portion 502*a*. The opening 512 in the cover portion 502*a* allows communication between the surface of the skin and a blood extraction chamber adjacent to a glucose detector 514, shown here in the shape of a strip. When in use, the device 500 is positioned so that the lancing assembly 508 is placed over the region on the surface of the skin from which the sample is to be obtained. In order to obtain the sample of blood, the cover portion 502*a* of the housing 502 of the device 500 is placed against the skin, whereby the seal allows a satisfactory vacuum to be effected. The switch is actuated, typically by being pressed, thereby activating the electronics, which starts the vacuum pump. The vacuum pump then provides a suction action. The suction action of the vacuum pump causes the skin circumscribed by the seal to become engorged with blood. Engorgement of the skin with blood is accompanied by a stretching of and rising up of the skin up to the opening 512.

After an appropriate period of time, which is typically pre-set by the programmer of the electronics, the lancing assembly 508 is triggered, thereby causing the lancet 516 to penetrate the skin that has risen up to the opening 512 and that is engorged with blood. The lancet 516 is preferably triggered automatically, by a solenoid valve (not shown) that causes a vacuum-actuated piston (not shown) to trigger the lancet 516. The remaining steps of the process relating to collection of a sample of blood are substantially similar to the steps described in the embodiment shown in FIGS. 1, 2, 3, and 4.

In the embodiment shown in FIG. 9, the glucose detector 514 is inserted into a slot 518 of the housing 502. The results obtained from the glucose detector 514 can be displayed on screen 520, typically a conventional liquid crystal digital display. The cover portion 502*a* is opened when the lancet 516 or glucose detector 514 is being replaced. The cover portion 502*a* is closed during the process of obtaining a sample of blood.

The relative positions of the vacuum pump, the battery, the electronics, the switch, the evacuation tube, the check valve, the solenoid valves, and the vacuum-actuated piston are substantially similar to the relative positions of these components as described in the embodiments shown in FIGS. 1 and 2.

Figure 10:
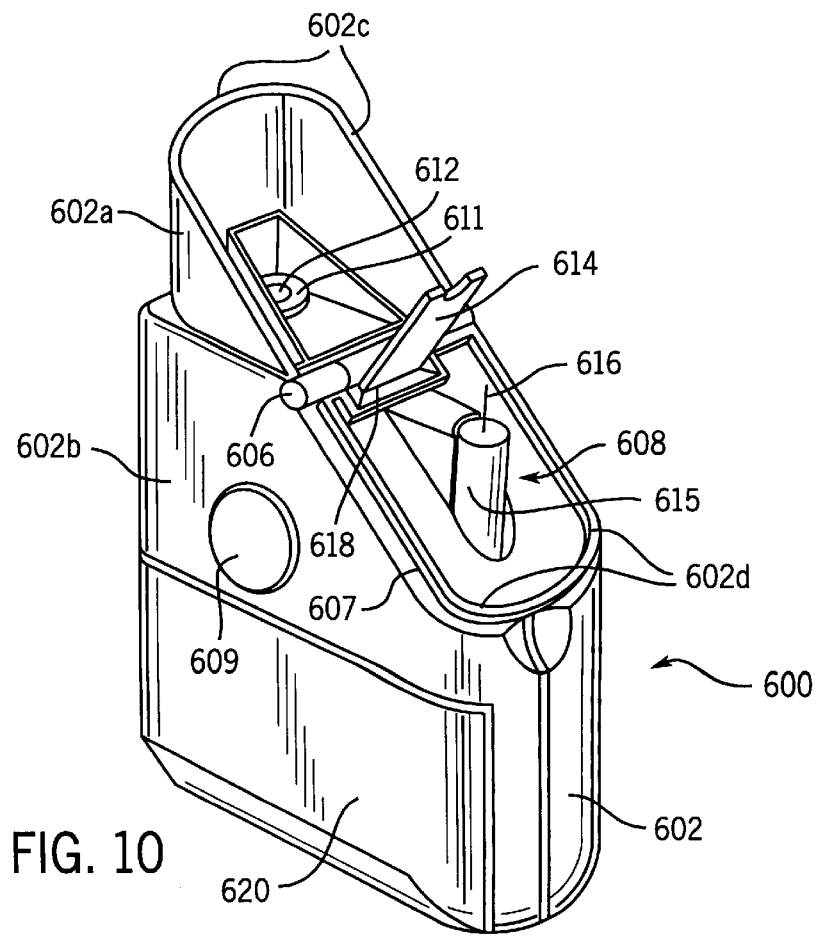
FIG. 10 is a perspective view of an embodiment of the apparatus of this invention. In this figure, the housing of the apparatus is open.

In FIG. 10, blood extraction device 600 comprises a housing 602. The housing 602 comprises a cover portion 602*a* that is attached to the remaining portion 602*b* of the housing 602 by a hinge 606. A gasket 607 is provided to seal the housing 602 when the cover portion 602*a* is closed. The cover portion 602*a* can be closed by pivoting it around the hinge 606. When the cover portion 602*a* is closed, edges 602*c* of the cover portion 602*a* tightly fit against edges 602*d* of the remaining portion 602*b* of the housing 602. Disposed within the housing 602 are a vacuum pump (not shown), a lancing assembly 608, a battery (not shown), and electronics (not shown). A switch 609 is provided to activate the electronics. The vacuum pump is connected to the lancing assembly 608 by an evacuation tube (not shown). A check valve (not shown) is placed between the vacuum pump and the lancing assembly 608.

During the process of obtaining the sample, the cover portion 602*a* is closed. The cover portion 602*a* of the housing 602 of the device 600 that contacts the skin is equipped with a seal 611. The seal 611 surrounds an opening 612 in the cover portion 602*a*. The opening 612 in the cover portion 602*a* allows communication between the surface of the skin and a blood extraction chamber adjacent to a glucose detector 614, shown here in the shape of a strip. When in use, the device 600 is positioned so that the lancing assembly 608 is placed over the region on the surface of the skin from which the sample is to be obtained. In order to obtain the sample of blood, the cover portion 602*a* of the housing 602 of the device 600 is placed against the skin, whereby the seal allows a satisfactory vacuum to be effected. The switch is actuated, typically by being pressed, thereby activating the electronics, which starts the vacuum pump. The vacuum pump then provides a suction action. The suction action of the vacuum pump causes the skin circumscribed by the seal to become engorged with blood. Engorgement of the skin with blood is accompanied by a stretching of and rising up of the skin up to the opening 612. After an appropriate period of time, which is typically pre-set by the programmer of the electronics, the lancing assembly 608 is triggered, thereby causing the lancet 616 to penetrate the skin that has risen up to the opening 612 and that is engorged with blood. The lancet 616 is preferably triggered automatically, by a solenoid valve (not shown) that causes a vacuum-actuated piston (not shown) to trigger the lancet 616. The remaining steps of the process relating to collection of a sample of blood are substantially similar to the steps described in the embodiment shown in FIGS. 1, 2, 3, and 4.

In the embodiment shown in FIG. 10, the glucose detector 614 is inserted into a slot 618 of the housing 602. The results obtained from the glucose detector 614 can be displayed on screen 620, typically a conventional liquid crystal digital display. The cover portion 602a is opened when the lancet 616 or glucose detector 614 is being replaced. The cover portion 602a is closed during the process of obtaining a sample of blood.

The relative positions of the vacuum pump, the battery, the electronics, the switch, the evacuation tube, the check valve, the solenoid valves, and the vacuum-actuated piston are substantially similar to the relative positions of these components as described in the embodiments shown in FIGS. 1 and 2.

In each of the embodiments shown in the foregoing FIGS. 5, 6, 7, 8, 9, and 10, the housing, vacuum pump, lancing assembly, battery, electronics, evacuation tube, check valve, nosepiece, seal, opening, blood extraction chamber, lancet, and solenoid valve can be made of the same materials as the corresponding components of the apparatus shown in FIGS. 1, 2, and 3. The gaskets 104, 207, 307, 407, 507, and 607 can be made of the same material as the seal. The components shown in the foregoing FIGS. 5, 6, 7, 8, 9, and 10 function in the same manner as do the corresponding components of the apparatus shown in FIGS. 1, 2, and 3.

It should be noted that the designs of the various housings shown in FIGS. 5, 6, 7, 8, 9, and 10 can be modified without substantially affecting the functioning of the components disposed within the housing or on the surface of the housing. For example, the shapes of the housings, the shapes of the door portions of the housings, the shapes of the cover portions of the housings, and the shapes of the remaining portions of the housings can be modified without departing from the scope and spirit of this invention.

This invention provides numerous advantages over blood extraction devices of the prior art. Among these advantages are the following:

1. Ability to use parts of the body, other than the finger, as a site for the extraction of blood;

2. Reduction of pain by eliminating the need to lance the finger;

3. Increase in speed of collection of blood samples by means of pre-treatment comprising a combination of stretching of the skin in conjunction with heat or vacuum or both heat and vacuum;

4. Incorporation of glucose detector in apparatus for extracting the blood sample.

The following examples illustrate various features of the present invention but is not intended to in any way limit the scope of the invention as set forth in the claims. In the following examples, the term "pierce" and forms thereof and the term "puncture" and forms thereof are used interchangeably. Although the expression "glucose detector" is used herein, one of ordinary skill in the art will recognize that the apparatus and methods of the present invention can also be used to perform other diagnostic tests.

EXAMPLES

Example 1

This example illustrates that greater volumes of blood can be extracted and collected by applying a vacuum, pulsed or continuous, after piercing than can be extracted and collected when no vacuum is applied. No vacuum was applied prior to piercing.

Each of four people had his forearm (dorsal forearm) punctured four times (at four different positions on the forearm) with a "BD ULTRA-FINE" lancet in a "MEDISENSE" lancet assembly (Model no. 97101) at two different levels of vacuum (−2.5 psig and −5.0 psig) and for each different vacuum pulsing frequencies (0, 0.2, 0.8, 3.2, 12.8, 25, 100 hertz). The vacuum was applied with a pipette tip having a diameter of 8 mm ("RAININ RT-200"). Four control runs without a vacuum were also carried out (one puncture per person). A total of 60 punctures per person were carried out. Accordingly, it can be seen that a total of 240 runs were carried out.

The vacuum was applied for a duration of 30 seconds after puncturing. Blood was collected into capillary tubes. In the control runs, the samples were extracted and collected 30 seconds after puncturing. The amount of blood collected was determined by measuring the length of blood in the tubes. The percentage of collections in which the volume of blood collected exceeded 1.0 μL was calculated. Sensation of pain was also recorded. The following pain scores were used:

Pain of 1=person did not feel anything or not sure if anything was felt

Pain of 2=person felt definite prick, not as painful as piercing of finger by standard finger lancet Pain of 3=person felt definite pain, approximately equal to a piercing of finger by standard finger lancet Blood collection results are set forth in TABLE I.

TABLE I

| Frequency (hertz) | Average volume of blood sample collected at −2.5 psig (μL) | Percent of samples having >1 μL of blood collected at −2.5 psig | Average volume of blood sample collected at −5.0 psig (μL) | Percent of samples having >1 μL of blood collected at −5.0 psig |
|---|---|---|---|---|
| 0 (Continuous) | 1.6 | 69 | 3.1 | 94 |
| 0.2 | 1.1 | 44 | 3.0 | 94 |
| 0.8 | 1.1 | 63 | | 75 |
| 3.2 | 1.5 | 56 | 3.8 | 75 |
| 12.8 | 1.8 | 75 | 3.1 | 100 |
| 25 | 2.3 | 75 | 3.2 | 94 |
| 100 | 2.4 | 81 | 2.7 | 88 |

With no vacuum, average volume of blood collected was 0.8 μL and 31% of the samples collected contained more than 1 μL. The pain results were as follows:

pain of 1=81% pain of 2=17% pain of 3=2%

The control runs (no vacuum) provided much lower volumes of blood collected than did the runs where vacuum was applied. Increased vacuum resulted in higher volumes of blood extracted. The pain was minimal, with only 2% of the punctures resulting in pain comparable to that resulting from a piercing of the finger.

Example 2

This example illustrates that application of vacuum prior to piercing as well as after piercing results in a greater volume of blood extracted than does the application of vacuum only after piercing.

Each of four people had his forearm (dorsal forearm, middle of forearm) punctured sixteen times (at sixteen different positions on the forearm) with a "BD ULTRA-FINE" lancet in a modified "MEDISENSE" lancet assembly at four different levels of vacuum. The four levels of vacuum used were −2.5, −5.0, −7.5, and −10.0 psig. The "MEDISENSE" lancet device was modified to allow vacuum to be pulled through the lancet assembly. Four punctures per person were carried out at each of the four levels of continuous vacuum. Accordingly, it can be seen that a total of 64 runs were carried out.

Prior to puncturing, the vacuum was applied for a period of 30 seconds; subsequent to puncturing, the vacuum was applied for a period of 30 seconds. The skin was under vacuum at the time the lancet was triggered. After the lancet was triggered, the lancet assembly was removed, and the vacuum was used to apply the same level of vacuum that had been used for the vacuum prior to puncturing. The vacuum, both prior to puncturing and subsequent to puncturing, was applied with a pipette tip having a diameter of 8 mm ("RAININ RT-200"). The pipette tip of the vacuum device was held level to the plane of the skin. Blood was then collected into capillary tubes. The amount of blood collected was determined by measuring the length of blood in the tubes. The percentage of collections in which the volume of blood collected exceeded 1.0 µL was calculated. Sensation of pain was also recorded. Blood collection results are set forth in TABLE II.

TABLE II

| Vacuum level (psig) | Average volume of blood sample collected (µL) | Percent of samples having >1 µL of blood collected |
|---|---|---|
| −2.5 | 4.6 | 94 |
| −5.0 | 7.8 | 100 |
| −7.5 | 9.2 | 100 |
| −10.0 | 14.0 | 100 |

The pain results were as follows:
pain of 1=58%
pain of 2=31%
pain of 3=11%

A nearly linear relationship between level of vacuum and volume of blood collected was observed. The average volume of blood collected with vacuum applied prior and after piercing was approximately twice that collected with vacuum applied only after piercing without vacuum applied prior to piercing. See the results of Example 1 for this comparison (7.8 µL vs. 3.1 µL). The volume of blood collected was always above 1 µL for all levels of vacuum, except −2.5 psig.

Example 3

This example illustrates that localized heating of the area to be pierced followed by vacuum after piercing results in a greater volume of blood being extracted than does extraction with only vacuum after piercing.

Each of four people had his forearm (dorsal forearm, middle of forearm) punctured eight times (at eight different positions on the forearm) with a "BD ULTRA-FINE" lancet in a "MEDISENSE" lancet assembly with heat applied (45° C.) prior to piercing for two different time periods, 15 seconds and 60 seconds. A total of 32 runs were carried out, 16 runs where the pre-heating duration was 15 seconds and 16 runs where the pre-heating duration was 60 seconds.

Heat was applied with a heating block, which was an aluminum block having a square face covered with a "KAPTON" film heater element controlled by an "OMEGA" DP41 temperature controller using a T-type thermocouple. Vacuum was applied after each puncturing for 30 seconds at −5.0 psig. Blood was collected into capillary tubes. The amount of blood collected was determined by measuring the length of blood in the tubes. The percentage of collections in which the volume of blood collected exceeded 1.0 µL was calculated. Pain was also tracked. Blood collection results are set forth in TABLE III.

TABLE III

| Pre-piercing heating duration (seconds) | Average volume of blood samples collected (µL) | Percent of samples having >1 µL of blood collected |
|---|---|---|
| 15 | 6.91 | 94 |
| 60 | 11.6 | 100 |

The pain results were as follows:
pain of 1=91%
pain of 2=9%
pain of 3=0%

The average volume of blood collected using a pre-heating duration of 15 seconds was more than twice the average volume of blood collected at a post-puncturing vacuum level of −5.0 psig., with no pre-heating. See the results of Example 1 for this comparison (6.91 µL vs. 3.1 µL). The average volume of blood collected using a pre-heating duration of 60 seconds was approximately four times the average volume of blood collected at a post-puncturing vacuum level of −5.0 psig, with no pre-heating. See the results of Example 1 for this comparison (11.6 µL vs. 3.1 µL).

Example 4

This example illustrates the effect that stretching the skin upwardly with a vacuum has on the extraction of blood.

Each of four people had his forearm (dorsal forearm, middle of forearm) punctured eight times (at eight different positions on the forearm) with a "BD ULTRA-FINE" lancet in a "MEDISENSE" lancet assembly. Vacuum was applied for a period of 30 seconds prior to puncturing at −5.0 psig using two different vacuum fixtures. The first fixture was a 15 mm diameter vacuum fixture (i.e., a hollow cylindrical tube) used without a net strung across the opening of the tube. The second fixture was a 15 mm diameter vacuum fixture (i.e., a hollow cylindrical tube) used with a net strung across the opening of the tube. The net prevented skin from being raised up into the vacuum fixture. The same vacuum fixture used prior to puncturing was applied for a period of 30 seconds after puncturing. The fixture was held level with the plane of the skin. Four punctures were carried out per person per condition (without net, with net). Accordingly, it can be seen that a total of 32 runs were carried out. Blood was collected into capillary tubes. The amount of blood collected was determined by measuring the length of blood in the tubes. The percentage of collections in which the volume of blood collected exceeded 1.0 µL was calculated. Sensation of pain was also recorded. Blood collection results are set forth in TABLE IV.

TABLE IV

| Net across nosepiece | Average volume of blood sample collected (µL) | Percent of samples having >1 µL of blood collected |
|---|---|---|
| No | 5.2 | 87 |
| Yes | 0.6 | 19 |

The pain results were as follows:
pain of 1=94%
pain of 2=6%
pain of 3=0%

The magnitude of the difference in volume of blood collected and success rates (i.e., percent of samples having >1

µL of blood collected) between the condition of stretching the skin in combination with a vacuum and the condition of not stretching the skin in combination with a vacuum was unexpected. The pain scores were low. This example demonstrates that the combination of skin stretching and applied vacuum significantly increased the volume of blood extracted.

Example 5

This example illustrates the effect the area of the extraction site has on the volume of blood collected.

Each of four people had his forearm (dorsal forearm, middle of forearm) punctured at 32 different positions on the forearm with a "BD ULTRA-FINE" lancet in a modified "MEDISENSE" lancet assembly. The "MEDISENSE" lancet assembly had been modified with a more powerful spring and a port had been added.

Vacuum was applied for less than five seconds prior to puncturing. The forearm was punctured under a vacuum of either −5.0 psig or −7.5 psig. The vacuum applied was maintained for 30 seconds after puncturing. The diameter of the pipette tip used to apply vacuum after puncturing was varied, with diameters of 4,6, 8, and 10 mm being used. Four punctures per condition (diameter, vacuum level) were carried out per person. Accordingly, it can be seen that a total of 128 runs were carried out. Blood was collected into capillary tubes. The amount of blood collected was determined by measuring the length of blood in the tubes. The percentage of collections in which the volume of blood collected exceeded 1.0 µL was calculated. Sensation of pain was also recorded. Blood collection results are set forth in TABLE VA and VB.

TABLE VA vacuum level = −5.0 psig

| Vacuum diameter (mm) | Average volume of blood sample collected (µL) | Percent of samples having >1 µL of blood collected |
|---|---|---|
| 4 | 0.3 | 0 |
| 6 | 1.7 | 69 |
| 8 | 3.4 | 94 |
| 10 | 4.1 | 100 |

TABLE VB vacuum level = −7.5 psig

| Vacuum diameter (mm) | Average volume of blood sample collected (µL) | Percent of samples having >1 µL of blood collected |
|---|---|---|
| 4 | 0.8 | 25 |
| 6 | 3.1 | 94 |
| 8 | 3.4 | 81 |
| 1 | 6.3 | 94 |

The pain results were as follows:
pain of 1=89%
pain of 2=10%
pain of 3=1%

The volume of blood collected and success rates (i.e., percent of samples having >1 µL of blood collected) were found to vary directly with the area of skin raised up into the device by the vacuum. A much greater volume of skin was raised up into the larger diameter pipette tip than into the smaller diameter pipette tips.

Example 6

This example illustrates that a plastic multiple point lancet can be used with heat and vacuum to collect a useful amount of blood.

Each of four people had his forearm (dorsal forearm, middle of forearm) punctured sixteen times (at sixteen different positions on the forearm) with a Greer Derma PIK® System for allergy testing (Greer Laboratories, Inc., Lenoir, N.C. 28645) modified to fit into a "MEDISENSE" lancet assembly. Pre-heating was carried out at approximately 40° C. and 45° C. for 15 and 60 seconds prior to puncturing. Four punctures were carried out per condition (temperature, time) per person. Accordingly, it can be seen that a total of 64 runs were carried out.

Heat was applied with a heating block, which comprised an aluminum block having one face covered with a "KAPTON" film heater element controlled by an "OMEGA" DP41 temperature controller using a T-type thermocouple and the opposite face in contact with the larger base of a frustum of a cone made of copper. The larger base of the frustum had a diameter of 0.50 in. The height of the frustum was 0.50 in. The smaller base of the frustum had a diameter of 0.35 in. The smaller base had a cylindrical opening having a diameter of 0.125 in. The cylindrical opening had a common axis with the frustum. The cylindrical opening reduced the heating surface of the copper frustum. Vacuum (−5.0 psig) was applied for a period of 30 seconds after puncturing. The vacuum in contact with the skin was formed by a pipette tip having a diameter of 8 mm. The pipette tip was held level with the plane of the skin. Blood was collected into capillary tubes. The amount of blood collected was determined by measuring the length of blood in the tubes. The percentage of collections in which the volume of blood collected exceeded 1.0 µL was calculated. Sensation of pain was also recorded. Blood collection results are set forth in TABLE VI.

TABLE VI

| Temperature (° C.)/Time (seconds) | Average volume of blood sample collected (µL) | Percent of samples having >1 (µL) of blood collected |
|---|---|---|
| 40/15 | 2.4 | 31 |
| 40/60 | 2.6 | 50 |
| 45/15 | 2.3 | 56 |
| 45/60 | 5.2 | 81 |

The pain results were as follows:
pain of 1=100%
pain of 2=0%
pain of 3=0%

This example demonstrates that a blood extraction process employing a multi- point plastic lancet, pre-piercing heating, skin stretching, and post-piercing vacuum can extract at least 1 µL of blood at least 50% of the time.

Example 7

Multiple-layer elements comprising the following layers, from top to bottom, were prepared:
(1) meter-contactable layer
(2) detecting layer
(3) overcoat layer
(4) blood-transporting layer
(5) covering layer The arrangement of the layers is shown schematically in FIGS. 11A and 11B. However, the overcoat layer is substantially coplanar with the blood-transporting layer as shown in FIG. 18. The meter-contactable layer 1114 was about 5.5 mm wide and about 40 mm long. The meter-contactable layer was made from polyvinyl chloride. A 1.5 mm diameter opening was punched in the meter-contactable layer. The detecting layer 1110 was screen printed on the meter-contactable layer. Across the opening in the meter-contactable layer was placed a layer of mesh, which served as the blood-transporting layer 1108. The mesh was the mesh previously identified as NY151 HC. The detecting layer 1110 was the type of detecting layer described in U.S. Pat. No. 5,682,884. The overcoat layer 1123 was screen printed about the periphery of the layer of mesh. The covering layer 1102 was about 5.5 mm wide and somewhat shorter than the meter-contactable layer so that the electrical contacts 1110a of the detecting layer 1110 would be exposed. The covering layer was made from polyester. A 2.5 mm by 3.7 mm oval opening in the covering layer was punched prior to assembly of the multiple-layer element.

The multiple-layer element was placed in the apparatus as shown in FIGS. 19A, 19B, 19C, and 19D. A vacuum of −7.5 psig was applied. The apparatus was placed in contact with the forearm of a volunteer who was diabetic. See FIG. 19A. The skin of the forearm was stretched and it raised up into the nosepiece, where it came near to or into contact with the covering layer 1102 of the multiple-layer element. See FIG. 19B. After the vacuum had been applied for five seconds, the lancet was fired into the skin by means of a spring-powered lancet assembly. The lancet passed through the opening 1116 in the meter-contactable layer 1114 and the opening 1104 in the covering layer 1102. See FIG. 19C. The lancet was retracted and blood began to emerge from the forearm of the diabetic volunteer. The vacuum aided in the extraction of blood until the blood reached the layer of mesh 1108. See FIG. 19D. The blood was then transported along the mesh until it reached the detecting layer 1110 of the multiple-layer element. When the blood reached the detecting layer of the multiple-layer element, an electrical current was generated. This current was used to determine when to release the vacuum. The electrical current was also an indication of the level of glucose in the blood of the volunteer.

Figure 20:
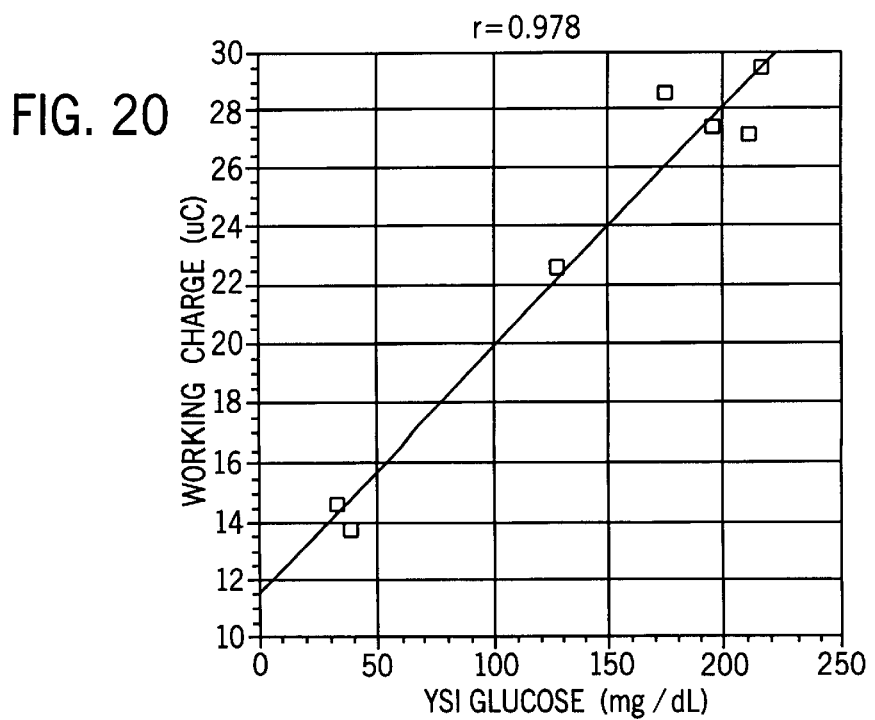
FIG. 20 is a graph illustrating average electrical charge as a function of glucose level in the blood.

Seven diabetic volunteers were tested as described in the previous paragraph. The time required for the multiple-layer element to fill after the lancing operation was recorded. The multiple-layer element was considered to be filled when a current of 1.5 $\mu A$ was generated. The vacuum was then released and the current was recorded for 20 seconds. During the last five seconds of the 20 second measurement period, the current was integrated. The integrated current (i.e., charge) was recorded. The lancing procedure and data collection were repeated four times per volunteer. All 28 lancing procedures resulted in blood filling the multiple-layer element in less than 40 seconds. The average time required to fill the multiple-layer element was 7 seconds. FIG. 20 shows the average charge of the four trials as a function of the level of glucose in the blood of each volunteer. The level of glucose was determined by withdrawing blood from a finger and measuring the level of glucose on a YSI 2300 Glucose analyzer. The charge increased linearly with the level of glucose in the blood of the volunteer. The volunteers were asked to rate the pain of the forearm lancet. The pain of the forearm lancet was found to be lower than the pain of the finger lancet, as shown in FIG. 21.

Example 8

Multiple-layer elements comprising the following layers, from top to bottom, were prepared:
(1) meter-contactable layer
(2) detecting layer
(3) overcoat layer
(4) - blood-transporting layer
(5) covering layer The arrangement of the layers is shown schematically in FIGS. 11A and 11B. However, the overcoat layer is substantially coplanar with the blood-transporting layer as shown in FIG. 18. The meter-contactable layer 1114 was about 5.5 mm wide and about 40 mm long. The meter-contactable layer was made from polyester. A 2.0 mm diameter opening was punched in the meter-contactable layer. The detecting layer 1110 was screen printed on the meter-contactable layer. Across the opening in the meter-contactable layer was placed a layer of mesh, which served as the blood-transporting layer 1108. The mesh was the mesh previously identified as NY151 HC. A section of the mesh (1.5 mm in diameter) was punched out by means of a hole punch. See FIG. 15. The detecting layer 1110 was the type of detecting layer described in U.S. Pat. No. 5,682,884. The overcoat layer 1123 was screen printed about the periphery of the layer of mesh. The covering layer 1102 was about 5.5 mm wide and somewhat shorter than the meter-contactable layer so that the electrical contacts 1110a of the detecting layer 1110 would be exposed. The covering layer was made from polyester. A 2.5 mm by 3.7 mm oval opening in the covering layer was punched prior to assembly of the multiple-layer element.

The multiple-layer element was placed in the apparatus as shown in FIGS. 19A, 19B, 19C, and 19D. A vacuum of −7.5 psig was applied. The apparatus was placed in contact with the forearm of a volunteer. See FIG. 19A. The skin of the forearm was stretched and it raised up into the nosepiece, where it came near to or into contact with the covering layer 1102 of the multiple-layer element. See FIG. 19B. After the vacuum had been applied for five seconds, the lancet was fired into the skin by means of a pneumatic lancing assembly of the type shown in FIGS. 11, 12, 13, and 14 of the copending application entitled METHOD AND APPARATUS FOR OBTAINING BLOOD FOR DIAGNOSTIC TESTS, Attorney's Docket No. 6005.US. P1, filed on even-date herewith, the entirety of which is incorporated herein by reference. The lancet passed through the opening 1116 in the meter-contactable layer 1114 and the opening 1104 in the covering layer 1102. See FIG. 19C. The lancet was retracted and blood began to emerge from the forearm of the volunteer. The vacuum aided in the extraction of blood until the blood reached the mesh 1108. See FIG. 19D.

The blood was then transported along the mesh until it reached the detecting layer 1110 of the multiple-layer element. When the blood reached the detecting layer of the multiple-layer element, an electrical current was generated. This current was used to determine when to release the vacuum.

Eight volunteers were tested as described in the previous paragraph.

The time required for the multiple-layer element to fill after the lancing operation was recorded. The multiple-layer element was considered to be filled when a current of 1.5 $\mu A$ was generated. The vacuum was then released and the integrated current was recorded. The lancing procedure and data collection were repeated four times per volunteer. Blood filled the multiple-layer element in less than 40 seconds for 97% of the tests. The average time required to fill the multiple-layer element was 15.9 seconds.

Example 9

Multiple-layer elements comprising the following layers, from top to bottom, were prepared:

(1) meter-contactable layer
(2) detecting layer
(3) overcoat layer
(4) blood-transporting layer
(5) covering layer The arrangement of the layers is shown schematically in FIGS. 11A and 11B. However, the overcoat layer is substantially coplanar with the blood-transporting layer as shown in FIG. 18. The meter-contactable layer 1114 was about 5.5 mm wide and about 40 mm long. The meter-contactable layer was made from polyester. Two types of meter-contactable layers were prepared. In the first type, one opening was punched in the meter-contactable layer. This opening had a diameter of 2.0 mm. No mesh was placed across this opening. See FIG. 16B. In the second type, two openings were punched in the meter-contactable layer. One opening had a diameter of 2.0 mm. The other opening had a diameter of 1.5 mm. The second opening was located 2 mm from the first opening. See FIG. 16A. The detecting layer 1110 was screen printed on the meter-contactable layer. Across the 1.5 mm opening in the meter-contactable layer was placed a layer of mesh, which served as the blood-transporting layer 1108. The mesh was the mesh previously identified as NY151 HC. The detecting layer 1110 was the type of detecting layer described in U.S. Pat. No. 5,682,884. The overcoat layer 1123 was screen printed about the periphery of the layer of mesh. The covering layer 1102 was about 5.5 mm wide and somewhat shorter than the meter-contactable layer so that the electrical contacts 1110a of the detecting layer 1110 would be exposed. The covering layer was made from polyester. A 2.5 mm by 3.7 mm oval opening in the covering layer was punched prior to assembly of the multiple-layer element.

The multiple-layer element was placed in the apparatus as shown in FIGS. 19A, 19B, 19C, and 19D. A vacuum of −7.5 psig was applied. The apparatus was placed in contact with the forearm of a volunteer. See FIG. 19A. The skin of the forearm was stretched and it raised up into the nosepiece, where it came near to or into contact with the covering layer 1102 of the multiple-layer element. See FIG. 19B. After the vacuum had been applied for five seconds, the lancet was fired into the skin by means of a pneumatic lancet assembly. This pneumatic lancet assembly was the assembly shown in FIGS. 16 and 17 of the copending application entitled METHOD AND APPARATUS FOR OBTAINING BLOOD FOR DIAGNOSTIC TESTS, Attorney's Docket No. 6005.US.P1, filed on evendate herewith, the entirety of which is incorporated herein by reference.

The lancet passed through the 2.0 mm opening 1116 in the meter-contactable layer 1114 and the opening 1104 in the covering layer 1102. See FIG. 19C. The lancet was retracted and blood began to emerge from the forearm of the volunteer. See FIG. 19D. As quickly as possible, the multiple-layer element was slid approximately 2 mm in the direction away from the electrical contacts. This type of movement is more fully described in copending application entitled METHOD AND APPARATUS FOR OBTAINING BLOOD FOR DIAGNOSTIC TESTS, Attorney's Docket No. 6005.US.P4, filed on evendate herewith, the entirety of which is incorporated herein by reference. The movement of the multiple-layer element caused the site of the opening in the skin to be in vertical alignment with the mesh 1108 of the multiple-layer element. In the case of the meter-contactable layer having two openings, this was the site of the opening 1122 that was 1.5 mm in diameter. The vacuum aided in the extraction of blood until the blood reached the mesh 1108. The blood was then transported along the mesh until it reached the detecting layer 1110 of the multiple-layer element. When the blood reached the detecting layer 1110 of the multiple-layer element, an electrical current was generated. This current was used to determine when to release the vacuum.

Nine non-diabetic volunteers were tested as described in the previous paragraph. Each volunteer was tested with each type of multiple-layer element. The time required for the multiple-layer element to fill after the lancing operation was recorded. The multiple-layer element was considered to be filled when a current of 1.5 $\mu$A was generated. The vacuum was then released. The lancing procedure and data collection were repeated eight times per volunteer per element. Blood filled the multiple-layer element having one opening in the meter-contactable layer in less than 40 seconds for 95% of the tests. Blood filled the multiple-layer element having two openings in the meter-contactable layer in less than 40 seconds for 96% of the tests. The average time required to fill the multiple-layer element having two openings in the meter-contactable layer was 14 seconds. The average time required to fill the multiple-layer element having one opening in the meter-contactable layer was 11 seconds.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for performing a diagnostic test utilizing a sample of blood, said method comprising the steps of:
   (a) forming an unobstructed opening in an area of skin from which said sample is to be extracted;
   (b) extracting said sample from said unobstructed opening in said area of said skin, with the aid of vacuum and stretching of the skin;
   (c) providing a multiple-layer article comprising:
      (i) a layer capable of receiving blood and transporting the blood received by means of chemically aided wicking;
      (ii) a layer capable of detecting the presence of analyte or measuring the amount of analyte in blood; and
      (iii) a layer that can be placed in contact with a meter, the meter-contactable layer overlying the blood-transporting layer, said layer (i) capable of transporting blood to said layer (ii).
   (d) allowing said extracted sample to be received by said blood-transporting layer and allowing said blood to be transported by means of chemically aided wicking to said layer capable of detecting the presence of analyte or measuring the amount of analyte in blood; and
   (e) determining the presence of analyte or measuring the amount of analyte in blood.

2. The method of claim 1, wherein no more than two microliters of blood are required for analyte determination.

3. The method of claim 1, wherein no more than one microliter of blood is required for analyte determination.

4. A method for performing a diagnostic test utilizing a sample of blood, said method comprising the steps of:
   (a) forming an unobstructed opening in an area of skin from which said sample is to be extracted;
   (b) extracting said sample from said unobstructed opening in said area of said skin, with the aid of vacuum and stretching of the skin;

(c) providing a multiple-layer article comprising:
  (i) a covering layer having an opening therein;
  (ii) a layer, overlying the covering layer, capable of receiving blood through the opening in the covering layer and transporting blood by means of chemically aided wicking;
  (iii) a layer that can be placed in contact with a meter, the meter-contactable layer overlying the blood-transporting layer; and
  (iv) a layer capable of detecting the presence of analyte or measuring the amount of analyte in blood, which layer is disposed between the covering layer and the meter-contactable layer and is capable of receiving blood from the blood-transporting layer.
(d) allowing said extracted sample to be received by said blood-transporting layer and allowing said blood to be transported by means of chemically aided wicking to said layer capable of detecting the presence of analyte or measuring the amount of analyte in blood; and
(e) determining the presence of analyte or measuring the amount of analyte in blood.

5. The method of claim 4, wherein no more than two microliters of blood are required for analyte determination.

6. The method of claim 4, wherein no more than one microliter of blood is required for analyte determination.

7. A method for performing a diagnostic test utilizing a sample of blood, said method comprising the steps of:
  (a) forming an unobstructed opening in an area of skin from which said sample is to be extracted;
  (b) extracting said sample from said unobstructed opening in said area of said skin, with the aid of vacuum and stretching of the skin;
  (c) providing a multiple-layer article comprising:
    (i) a covering layer;
    (ii) a layer, overlying said covering layer, that can be placed in contact with a meter; and
    (iii) a layer capable of detecting the presence of analyte or measures the amount of analyte in blood, which layer is disposed between said covering layer and said meter-contactable layer and is capable of receiving blood by means of capillary flow of blood between said covering layer and said meter-contactable layer, wherein said covering layer and said meter-contactable layer are spaced apart at a sufficient distance so that a capillary is formed between them;
  (d) allowing said extracted sample to be transported by means of capillary flow to said layer capable of detecting the presence of analyte or measuring the amount of analyte in blood; and
  (e) determining the presence of analyte or measuring the amount of analyte in blood.

8. The method of claim 7, wherein no more than two microliters of blood are required for analyte determination.

9. The method of claim 7, wherein no more than one microliter of blood is required for analyte determination.

* * * * *